(12) United States Patent
Andries et al.

(10) Patent No.: US 7,709,498 B2
(45) Date of Patent: *May 4, 2010

(54) QUINOLINE DERIVATIVES AS ANTIBACTERIAL AGENTS

(75) Inventors: Koenraad Jozef Lodewijk Marcel Andries, Beerse (BE); Anil Koul, Berchem (BE); Jérôme Emile Georges Guillemont, Ande (FR); Elisabeth Therese Jeanne Pasquier, Le Neubourg (FR)

(73) Assignee: Janssen Pharmaceutica N.V. (BE)

( * ) Notice: Subject to any disclaimer, the term of this patent is extended or adjusted under 35 U.S.C. 154(b) by 1030 days.

This patent is subject to a terminal disclaimer.

(21) Appl. No.: 11/296,918

(22) Filed: Dec. 8, 2005

(65) Prior Publication Data
US 2006/0281741 A1 Dec. 14, 2006

(30) Foreign Application Priority Data
Jun. 8, 2005 (EP) ................. 05105023

(51) Int. Cl.
C07D 215/38 (2006.01)
(52) U.S. Cl. ........................ 514/312; 546/156
(58) Field of Classification Search ............ 546/156; 514/227, 312
See application file for complete search history.

(56) References Cited

U.S. PATENT DOCUMENTS

| 5,965,572 A | 10/1999 | Ellis et al. |
| 7,498,343 B2 * | 3/2009 | Van Gestel et al. ......... 514/312 |
| 2005/0148581 A1 * | 7/2005 | Van Gestel et al. ....... 514/227.8 |

FOREIGN PATENT DOCUMENTS

| RU | 2126000 C1 | 2/1999 |
| WO | WO 94/10163 A | 5/1994 |
| WO | WO 95/06047 | 3/1995 |
| WO | WO 99/37635 A | 7/1999 |
| WO | WO 00/34265 A | 6/2000 |
| WO | WO 2004/011436 A | 2/2004 |
| WO | WO 2005/070924 A1 | 8/2005 |
| WO | WO 2005/117875 A1 | 12/2005 |

OTHER PUBLICATIONS

Wise, Antimicrobial agents and Chemotherapy, vol. 32(8), pp. 1251-1256, 1988.*

Andries, Koen; A Diarylquinoline Drug Active on the ATP Synthase of Mycobacterium Tuberculosis, Science vol. 307 Jan. 14, 2005 pp. 223-227.

* cited by examiner

Primary Examiner—D. Margaret Seaman

(57) ABSTRACT

The present invention relates to a method for the treatment of a bacterial infection comprising administering a therapeutically effective amount of a compound of formula

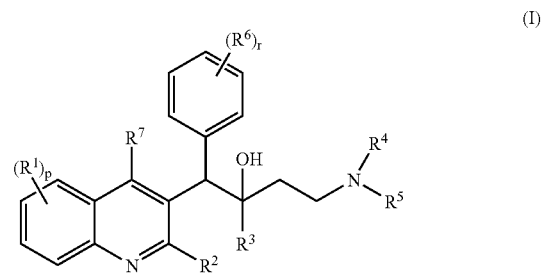

(I)

or a pharmaceutically acceptable acid or base addition salt thereof, a stereochemically isomeric form thereof or a N-oxide form thereof, wherein $R^1$ is hydrogen, halo, polyhalo$C_{1-6}$alkyl, $C_{1-6}$alkyl, Ar or Het; p is an integer equal to 1 or 2; $R^2$ is $C_{1-6}$alkyloxy, $C_{1-6}$alkyloxy$C_{1-6}$alkyloxy or $C_{1-6}$alkylthio; $R^3$ is Ar, Het or Het$^1$; $R^4$ and $R^5$ each independently are hydrogen, $C_{1-6}$alkyl or benzyl; or $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, each of said rings may optionally be substituted with $C_{1-6}$alkyl, halo, polyhalo$C_{1-6}$alkyl, hydroxy, hydroxy$C_{1-6}$alkyl, $C_{1-6}$alkyloxy, amino, mono- or di($C_{1-6}$alkyl)amino, $C_{1-6}$alkylthio, $C_{1-6}$alkyloxy$C_{1-6}$alkyl, $C_{1-6}$alkylthio$C_{1-6}$alkyl or pyrimidinyl; $R^6$ is hydrogen, halo, polyhalo$C_{1-6}$alkyl, $C_{1-6}$alkyl, $C_{1-6}$alkyloxy, $C_{1-6}$alkylthio; or two vicinal $R^6$ radicals may be taken together to form a bivalent radical of formula —CH=CH—CH=CH—; r is an integer equal to 1 or 2; $R^7$ is hydrogen, $C_{1-6}$alkyl, Ar, Het or Het$^1$; provided that to bacterial infection is other than a Mycobacterial infection.

35 Claims, No Drawings

QUINOLINE DERIVATIVES AS ANTIBACTERIAL AGENTS

This application claims priority of EP 05/103023.5, filed Jun. 8, 2005.

The present invention relates to the use of quinoline derivatives for the manufacture of a medicament for the treatment of a bacterial infection.

Resistance to first-line antibiotic agents is an emerging problem. Some important examples include penicillin-resistant *Streptococcus pneumoniae*, vancomycin-resistant enterococci, methicillin-resistant *Staphylococcus aureus*, multi-resistant salmonellae.

The consequences of resistance to antibiotic agents are severe. Infections caused by resistant microbes fail to respond to treatment, resulting in prolonged illness and greater risk of death. Treatment failures also lead to longer periods of infectivity, which increase the numbers of infected people moving in the community and thus exposing the general population to the risk of contracting a resistant strain infection. Hospitals are a critical component of the antimicrobial resistance problem worldwide. The combination of highly susceptible patients, intensive and prolonged antimicrobial use, and cross-infection has resulted in infections with highly resistant bacterial pathogens.

Self-medication with antimicrobials is another major factor contributing to resistance. Self-medicated antimicrobials may be unnecessary, are often inadequately dosed, or may not contain adequate amounts of active drug.

Patient compliance with recommended treatment is another major problem. Patients forget to take medication, interrupt their treatment when they begin to feel better, or may be unable to afford a full course, thereby creating an ideal environment for microbes to adapt rather than be killed.

Because of the emerging resistance to multiple antibiotics, physicians are confronted with infections for which there is no effective therapy. The morbidity, mortality, and financial costs of such infections impose an increasing burden for health care systems worldwide.

Therefore, there is a high need for new compounds to treat bacterial infections, especially for the treatment of infections caused by resistant strains.

WO 2004/011436 discloses substituted quinoline derivatives having activity against *Mycobacteria*, in particular against *Mycobacterium tuberculosis*. One particular compound of these substituted quinoline derivatives is described in Science (2005), 307, 223-227.

It has now been found that quinoline derivatives described in WO 2004/011436 also show activity against other bacteria than *Mycobacteria*.

Therefore, the present invention relates to the use of a compound for the manufacture of a medicament for the treatment of a bacterial infection, said compound being a compound of formula

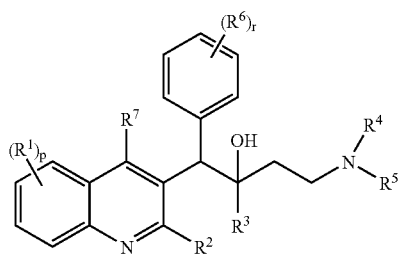

(I)

a pharmaceutically acceptable acid or base addition salt thereof, a stereochemically isomeric form thereof or a N-oxide form thereof, wherein $R^1$ is hydrogen, halo, polyhalo$C_{1-6}$alkyl, $C_{1-6}$alkyl, Ar or Het;

p is an integer equal to 1 or 2;

$R^2$ is $C_{1-6}$alkyloxy, $C_{1-6}$alkyloxy$C_{1-6}$alkyloxy or $C_{1-6}$alkylthio;

$R^3$ is Ar, Het or Het$^1$;

$R^4$ and $R^5$ each independently are hydrogen, $C_{1-6}$alkyl or benzyl; or $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, each of said rings may optionally be substituted with $C_{1-6}$alkyl, halo, polyhalo$C_{1-6}$ alkyl, hydroxy, hydroxy$C_{1-6}$alkyl, $C_{1-6}$alkyloxy, amino, mono- or di($C_{1-6}$alkyl)amino, $C_{1-6}$alkylthio, $C_{1-6}$alkyloxy$C_{1-6}$alkyl, $C_{1-6}$alkylthio$C_{1-6}$alkyl or pyrimidinyl;

$R^6$ is hydrogen, halo, polyhalo$C_{1-6}$alkyl, $C_{1-6}$alkyl, $C_{1-6}$alkyloxy, $C_{1-6}$alkylthio; or two vicinal $R^6$ radicals may be taken together to form a bivalent radical of formula —CH=CH—CH=CH—;

r is an integer equal to 1 or 2;

$R^7$ is hydrogen, $C_{1-6}$alkyl, Ar, Het or Het$^1$;

Ar is a homocycle selected from the group of phenyl, naphthyl, acenaphthyl, tetrahydronaphthyl, each homocycle may optionally be substituted with 1, 2 or 3 substituents, each substituent independently selected from the group of hydroxy, halo, cyano, nitro, amino, mono- or di($C_{1-6}$alkyl)amino, $C_{1-6}$alkyl, polyhalo$C_{1-6}$alkyl, hydroxy$C_{1-6}$alkyl, $C_{1-6}$alkyloxy, polyhalo$C_{1-6}$alkyloxy, $C_{1-6}$alkyloxy$C_{1-6}$alkyl, carboxyl, $C_{1-6}$alkyloxycarbonyl, aminocarbonyl, morpholinyl and mono- or di($C_{1-6}$alkyl)aminocarbonyl;

Het is a monocyclic heterocycle selected from the group of N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; each monocyclic heterocycle may optionally be substituted with 1, 2 or 3 substituents, each substituent independently selected from the group of halo, hydroxy, $C_{1-6}$alkyl, polyhalo$C_{1-6}$alkyl, hydroxy$C_{1-6}$alkyl, $C_{1-6}$alkyloxy, $C_{1-6}$alkyloxy$C_{1-6}$alkyl or Ar—C(=O)—;

Het$^1$ is a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each bicyclic heterocycle may optionally be substituted with 1, 2 or 3 substituents, each substituent independently selected from the group of halo, hydroxy, $C_{1-6}$alkyl, polyhalo$C_{1-6}$alkyl, hydroxy$C_{1-6}$alkyl, $C_{1-6}$alkyloxy, $C_{1-6}$alkyloxy$C_{1-6}$alkyl or Ar—C(=O)—;

provided that the bacterial infection is other than a Mycobacterial infection.

The present invention also relates to a method of treating a bacterial infection in a mammal, in particular a warm-blooded mammal, more in particular a human, comprising administering an effective amount of a compound of the invention to the mammal.

As used hereinbefore or hereinafter $C_{1-6}$alkyl as a group or part of a group defines straight or branched chain saturated hydrocarbon radicals having from 1 to 6 carbon atoms such as methyl, ethyl, propyl, 1-methylethyl, butyl, pentyl, hexyl, 2-methylbutyl and the like.

As used hereinbefore or hereinafter, the term (=O) forms a carbonyl moiety when attached to a carbon atom.

The term halo is generic to fluoro, chloro, bromo and iodo. As used in the foregoing or hereinafter, polyhalo$C_{1-6}$alkyl as a group or part of a group is defined as mono- or polyhalo-substituted $C_{1-6}$alkyl, for example, methyl with one or more fluoro atoms, for example, difluoromethyl or trifluoromethyl, 1,1-difluoro-ethyl and the like. In case more than one halogen atoms are attached to an alkyl group within the definition of polyhalo$C_{1-6}$alkyl, they may be the same or different.

In the definition of Het or Het$^1$, or when $R^4$ and $R^5$ are taken together, it is meant to include all the possible isomeric forms of the heterocycles, for instance, pyrrolyl comprises 1H-pyrrolyl and 2H-pyrrolyl.

The Ar, Het or Het$^1$ listed in the definitions of the substituents of the compounds of formula (I) (see for instance $R^3$) as mentioned hereinbefore or hereinafter may be attached to the remainder of the molecule of formula (I) through any ring carbon or heteroatom as appropriate, if not otherwise specified. Thus, for example, when Het is imidazolyl, it may be 1-imidazolyl, 2-imidazolyl, 4-imidazolyl and the like.

Lines drawn from substituents into ring systems indicate that the bond may be attached to any of the suitable ring atoms.

When two vicinal $R^6$ radicals are taken together to form a bivalent radical of formula —CH=CH—CH=CH—, this means that the two vicinal $R^6$ radicals form together with the phenyl ring to which they are attached a naphthyl.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable addition salts as mentioned hereinabove or hereinafter are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylaamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The N-oxide forms of the present compounds are meant to comprise the compounds of formula (I) wherein one or several tertiary nitrogen atoms are oxidized to the so-called N-oxide.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

It will be appreciated that some of the compounds of formula (I) and their N-oxides or addition salts may contain one or more centres of chirality and exist as stereochemically isomeric forms.

The term "stereochemically isomeric forms" as used hereinbefore or hereinafter defines all the possible stereoisomeric forms which the compounds of formula (I), and their N-oxides, addition salts or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure.

In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond.

Stereochemically isomeric forms of the compounds of formula (I) are obviously intended to be embraced within the scope of this invention.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S-[R*,S*]. If "□" and "□" are used: the position of the highest priority substituent on the asymmetric carbon atom in the ring system having the lowest ring number, is arbitrarily always in the "□" position of the mean plane determined by the ring system. The position of the highest priority substituent on the other asymmetric carbon atom in the ring system relative to the position of the highest priority substituent on the reference atom is denominated "□", if it is on the same side of the mean plane determined by the ring system, or "□", if it is on the other side of the mean plane determined by the ring system.

The terms "erythro" and "threo" can also be used as relative stereochemical descriptors. When a molecule bears two asymmetric carbons, 4 stereoisomers of the molecule exist. These isomers can be grouped in two couples of two enantiomers. A difference between these two couples can be made using the notation erythro and threo (initially used for Sugar). The two asymmetric carbon atoms on the lateral chain of the present compounds, indicated by * in the structure below, are determinant for the stereochemistry of the molecules. The relative configuration of the molecules is indicated as erythro if the groups, after being classified according to priority rules (rules of Cahn, Ingold, Prelog), scroll in the same direction when observed in Newman projection. The relative configuration of the molecules is indicated as threo if the groups, after being classified according to priority rules (rules of Cahn, Ingold, Prelog), scroll in the opposite direction when observed in Newman projection.

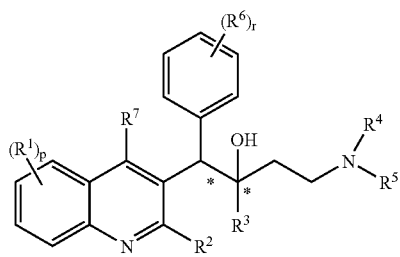

Instead of erythro and threo, the terms "syn" and "anti" can also be used as relative stereodescriptors for the two couples of two enantiomers. To determine whether a molecule is syn or anti, the main chain of the molecule is drawn in the common zigzag manner. If the two main substituents (substituents are ranked according to their priority (Cahn Ingold Prelog rules)) are on the same side of the plane defined by the main chain, the stereochemistry is indicated as syn. If the two main substituents are on the opposite side of the plane defined by the main chain, the stereochemistry is indicated as anti.

The stereodescriptors cis, trans, E, Z, R, S, erythro, threo, syn, anti are well known to a person skilled in the art. Reference is also made to J. Am. Chem. Soc., 1982, 104, 5521-5523, which is incorporated herein by reference.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s). Thus, when a compound of formula (I) is for instance specified as (αS,βR), this means that the compound is substantially free of the (αR,βS) isomer.

The compounds of formula (I) may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems,* 1985, pp. 112-176, and *Drugs,* 1985, 29, pp. 455-473.

Pro-drug forms of the pharmacologically-active compounds according to the invention will generally be compounds according to either formula (I), the pharmaceutically acceptable acid or base addition salts thereof, the stereochemically isomeric forms thereof, the tautomeric forms thereof and the N-oxide forms thereof, having an acid group which is esterified or amidated. Included in such esterified acid groups are groups of the formula —COOR$^x$, where R$^x$ is a $C_{1-6}$alkyl, phenyl, benzyl or one of the following groups:

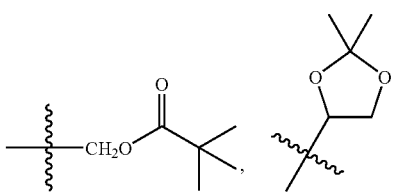

Amidated groups include groups of the formula —CONR$^y$R$^z$, wherein R$^y$ is H, $C_{1-6}$alkyl, phenyl or benzyl and R$^z$ is —OH, H, $C_{1-6}$alkyl, phenyl or benzyl.

Compounds according to the invention having an amino group may be derivatised with a ketone or an aldehyde such as formaldehyde to form a Mannich base. This base will hydrolyze with first order kinetics in aqueous solution.

Whenever used herein, the term "compounds of formula (I)" is meant to also include their N-oxide forms, their addition salts or their stereochemically isomeric forms. Of special interest are those compounds of formula (I) which are stereochemically pure.

A first interesting embodiment of the present invention relates to a compound of formula (I-a)

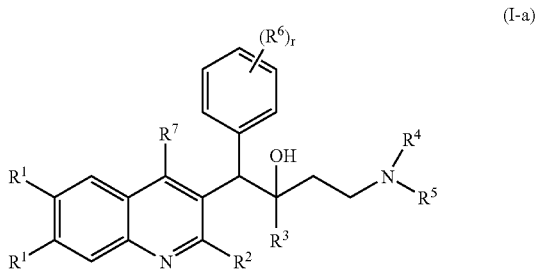

a pharmaceutically acceptable acid or base addition salt thereof, a stereochemically isomeric form thereof or a N-oxide form thereof.

A second interesting embodiment of the present invention relates to a compound of formula (I-b)

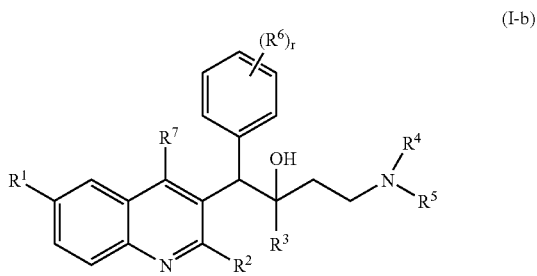

a pharmaceutically acceptable acid or base addition salt thereof, a stereochemically isomeric form thereof or a N-oxide form thereof.

A third interesting embodiment are the compounds of formula (I) or any subgroup thereof as mentioned hereinbefore as interesting embodiment wherein $R^1$ represents hydrogen, halo, $C_{1-6}$alkyl, Ar or Het; preferably hydrogen, halo, optionally substituted phenyl or Het; more preferably hydrogen, halo, optionally substituted phenyl, optionally substituted furanyl, or pyridinyl; even more preferably hydrogen, halo or optionally substituted phenyl; most preferred halo, such as for example bromo or chloro, in particular bromo.

A fourth interesting embodiment are the compounds of formula (I) or any subgroup thereof as mentioned hereinbefore as interesting embodiment wherein $R^1$ is halo, polyhalo$C_{1-6}$alkyl, Ar or Het; preferably halo, Ar or Het; more preferably halo, optionally substituted phenyl, or Het; even more preferably halo, phenyl, optionally substituted furanyl, or pyridinyl; most preferred halo or phenyl.

A fifth interesting embodiment are the compounds of formula (I) or any subgroup thereof as mentioned hereinbefore as interesting embodiment wherein $R^2$ is $C_{1-6}$alkyloxy or $C_{1-6}$alkylthio, in particular methoxy or methylthio; preferably $C_{1-6}$alkyloxy; more preferably methoxy.

A sixth interesting embodiment are the compounds of formula (I) or any subgroup thereof as mentioned hereinbefore as interesting embodiment wherein $R^3$ is Ar or Het or wherein $R^3$ is Ar or $Het^1$; preferably $R^3$ is Ar; more preferably optionally substituted phenyl or optionally substituted naphthyl; even more preferably phenyl optionally substituted with halo or $C_{1-6}$alkyloxy, or naphthyl optionally substituted with halo or $C_{1-6}$alkyloxy; most preferably phenyl optionally substituted with 1 or 2 halo, in particular fluoro, or naphthyl, in particular 1-naphthyl or 2-naphthyl.

A seventh interesting embodiment are the compounds of formula (I) or any subgroup thereof as mentioned hereinbefore as interesting embodiment wherein $R^4$ and $R^5$ each independently are hydrogen or $C_{1-6}$alkyl; or $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, each of said rings may optionally be substituted with $C_{1-6}$alkyl, halo, polyhalo$C_{1-6}$alkyl, hydroxy, hydroxy$C_{1-6}$alkyl, $C_{1-6}$alkyloxy, amino, mono- or di($C_{1-6}$alkyl)amino, $C_{1-6}$alkylthio, $C_{1-6}$alkyloxy$C_{1-6}$alkyl, $C_{1-6}$alkylthio$C_{1-6}$alkyl or pyrimidinyl; more preferably $R^4$ is $C_{1-6}$alkyl and $R^5$ is hydrogen or $C_{1-6}$alkyl; or $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, each of said rings may optionally be substituted with $C_{1-6}$alkyl, halo, polyhalo$C_{1-6}$alkyl, hydroxy, hydroxy$C_{1-6}$alkyl, $C_{1-6}$alkyloxy, amino, mono- or di($C_{1-6}$alkyl)amino, $C_{1-6}$alkylthio, $C_{1-6}$alkyloxy$C_{1-6}$alkyl, $C_{1-6}$alkylthio$C_{1-6}$alkyl or pyrimidinyl; even more preferably $R^4$ is $C_{1-6}$alkyl and $R^5$ is hydrogen or $C_{1-6}$alkyl; or $R^4$ and $R^5$ together and including the N to which they are attached may form a radical selected from the group of pyrrolyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, each of said rings may optionally be substituted with $C_{1-6}$alkyl, halo, polyhalo$C_{1-6}$alkyl, hydroxy, hydroxy$C_{1-6}$alkyl, $C_{1-6}$alkyloxy, amino, mono- or di($C_{1-6}$alkyl)amino, $C_{1-6}$alkylthio, $C_{1-6}$alkyloxy$C_{1-6}$alkyl, $C_{1-6}$alkylthio$C_{1-6}$alkyl or pyrimidinyl; most preferably $R^4$ is $C_{1-6}$alkyl, in particular methyl or ethyl, more in particular methyl, and $R^5$ is hydrogen or $C_{1-6}$alkyl, in particular methyl or ethyl, more in particular methyl.

An eighth interesting embodiment are the compounds of formula (I) or any subgroup thereof as mentioned hereinbefore as interesting embodiment wherein $R^4$ and $R^5$ each independently are hydrogen, $C_{1-6}$alkyl or benzyl; preferably $R^4$ and $R^5$ each independently are hydrogen or $C_{1-6}$alkyl; more preferably $R^4$ is $C_{1-6}$alkyl and $R^5$ is hydrogen or $C_{1-6}$alkyl; most preferred $R^4$ and $R^5$ are $C_{1-6}$alkyl, in particular methyl or ethyl, more in particular methyl.

A ninth interesting embodiment are the compounds of formula (I) or any subgroup thereof as mentioned hereinbefore as interesting embodiment wherein $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, each of said rings may optionally be substituted with $C_{1-6}$alkyl, halo, polyhalo$C_{1-6}$alkyl, hydroxy, hydroxy$C_{1-6}$alkyl, $C_{1-6}$alkyloxy, amino, mono- or di($C_{1-6}$alkyl)amino, $C_{1-6}$alkylthio, $C_{1-6}$alkyloxy$C_{1-6}$alkyl, $C_{1-6}$alkylthio $C_{1-6}$alkyl or pyrimidinyl; preferably $R^4$ and $R^5$ together and including the N to which they are attached may form a radical selected from the group of pyrrolyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, each of said rings may optionally be substituted with $C_{1-6}$alkyl, halo, polyhalo$C_{1-6}$alkyl, hydroxy, hydroxy$C_{1-6}$alkyl, $C_{1-6}$alkyloxy, amino, mono- or di($C_{1-6}$alkyl)amino, $C_{1-6}$alkylthio, $C_{1-6}$alkyloxy$C_{1-6}$alkyl, $C_{1-6}$alkylthio$C_{1-6}$alkyl or pyrimidinyl; more preferably $R^4$ and $R^5$ together and including the N to which they are attached may form a radical selected from the group of pyrrolyl, imidazolyl, pyrazolyl, triazolyl, piperidinyl, piperazinyl, morpholinyl and thiomorpholinyl, each of said rings may optionally be substituted with $C_{1-6}$alkyl, halo, polyhalo$C_{1-6}$alkyl, hydroxy, hydroxy$C_{1-6}$alkyl, $C_{1-6}$alkyloxy, amino, mono- or di($C_{1-6}$alkyl)amino, $C_{1-6}$alkylthio, $C_{1-6}$alkyloxy$C_{1-6}$alkyl, $C_{1-6}$alkylthio$C_{1-6}$alkyl or pyrimidinyl; even more preferably $R^4$ and $R^5$ together and including the N to which they are attached may form a radical selected from the group of imidazolyl, triazolyl, piperidinyl, piperazinyl, morpholinyl and thiomorpholinyl, each of said rings may optionally be substituted with $C_{1-6}$alkyl, halo, polyhalo$C_{1-6}$alkyl, hydroxy, hydroxy$C_{1-6}$alkyl, $C_{1-6}$alkyloxy, amino, mono- or di($C_{1-6}$alkyl)amino, $C_{1-6}$alkylthio, $C_{1-6}$alkyloxy$C_{1-6}$alkyl, $C_{1-6}$alkylthio$C_{1-6}$alkyl or pyrimidinyl; most preferred $R^4$ and $R^5$ together and including the N to which they are attached form imidazolyl.

Preferably, the substituents on the ring system when $R^4$ and $R^5$ are taken together, are selected from $C_{1-6}$alkyl, halo, polyhalo$C_{1-6}$alkyl, hydroxy, $C_{1-6}$alkyloxy, $C_{1-6}$alkylthio and pyrimidinyl; more preferably the substituents are selected from $C_{1-6}$alkyl or pyrimidinyl.

A tenth interesting embodiment are the compounds of formula (I) or any subgroup thereof as mentioned hereinbefore as interesting embodiment wherein $R^6$ is hydrogen, halo, polyhalo$C_{1-6}$alkyl or $C_{1-6}$alkyl; or two vicinal $R^6$ radicals may be taken together to form a bivalent radical of formula —CH=CH—CH=CH—; preferably $R^6$ is hydrogen, halo, polyhalo$C_{1-6}$alkyl or $C_{1-6}$alkyl; more preferably $R^6$ is hydrogen, halo or $C_{1-6}$alkyl; even more preferably $R^6$ is hydrogen or halo; most preferred $R^6$ is hydrogen.

An eleventh interesting embodiment are the compounds of formula (I) or any subgroup thereof as mentioned hereinbefore as interesting embodiment wherein $R^7$ is hydrogen.

A twelfth interesting embodiment are the compounds of formula (I) or any subgroup thereof as mentioned hereinbefore as interesting embodiment wherein r is an integer equal to 1.

A thirteenth interesting embodiment are the compounds of formula (I) or any subgroup thereof as mentioned hereinbefore as interesting embodiment wherein p is an integer equal to 1.

A fourteenth interesting embodiment are the compounds of formula (I) or any subgroup thereof as mentioned hereinbefore as interesting embodiment provided that when one $R^1$ is $C_{1-6}$alkyl then p is an integer equal to 2 and the other $R^1$ substituent is selected from halo, polyhalo$C_{1-6}$alkyl, $C_{1-6}$alkyl, Ar or Het.

A fifteenth interesting embodiment are the compounds of formula (I) or any subgroup thereof as mentioned hereinbefore as interesting embodiment wherein the compound is other than (αS,βR)-6-bromo-α-[2-(dimethylamino)ethyl]-2-methoxy-α-1-naphthalenyl-β-phenyl-3-quinolineethanol, a pharmaceutically acceptable acid or base addition salt thereof or a N-oxide form thereof.

A sixteenth interesting embodiment is the use of a compound of formula (I) or any subgroup thereof as mentioned hereinbefore as interesting embodiment for the manufacture of a medicament for the treatment of an infection with a gram-positive and/or a gram-negative bacterium.

A seventeenth interesting embodiment is the use of a compound of formula (I) or any subgroup thereof as mentioned hereinbefore as interesting embodiment for the manufacture of a medicament for the treatment of an infection with a gram-positive bacterium.

An eighteenth interesting embodiment is the use of the compounds of formula (I) or any subgroup thereof as mentioned hereinbefore as interesting embodiment for the manufacture of a medicament for the treatment of an infection with a gram-negative bacterium.

A nineteenth interesting embodiment is the use of a compound of formula (I) or any subgroup thereof as mentioned hereinbefore as interesting embodiment for the manufacture of a medicament for the treatment of a bacterial infection wherein the compound of formula (I) has a $IC_{90}$<15 µl/ml against at least one bacterium, in particular a gram-positive bacetrium, preferably a $IC_{90}$<10 µl/ml, more preferably a $IC_{90}$<5 µl/ml; the $IC_{90}$ value being determined as described hereinafter.

Also interesting compounds of the present invention are those compounds of formula (I) wherein one or more, preferably all, of the following definitions apply:

a) $R^1$ is hydrogen; $C_{1-6}$alkyl; halo, in particular bromo or chloro; phenyl; furanyl optionally substituted with hydroxy$C_{1-6}$alkyl; or pyridyl;

b) $R^2$ is $C_{1-6}$alkyloxy, in particular methoxy or ethoxy; $C_{1-6}$alkylthio, in particular methylthio; or $C_{1-6}$alkyloxy$C_{1-6}$alkyloxy;

c) $R^3$ is phenyl optionally substituted with 1 or 2 halo, in particular fluoro or chloro; naphthyl optionally substituted with 1 or 2 halo or $C_{1-6}$alkyloxy; thienyl; piperidinyl substituted with Ar—C(=O); 2,3-dihydrobenzo[1,4]dioxinyl; benzo[1,3]dioxolyl; or acenaphthyl;

d) $R^4$ and $R^5$ are each independently hydrogen; $C_{1-6}$alkyl; benzyl; or $R^4$ and $R^5$ together and including the N to which they are attached may form a radical selected from imidazolyl; pyrazinyl substituted with $C_{1-6}$alkyl; piperazinyl substituted with $C_{1-6}$alkyl; piperazinyl substituted with pyrimidinyl; piperidinyl; thiomorpholinyl; morpholinyl; pyrrolidinyl; or triazolyl;

e) $R^6$ is hydrogen; halo, in particular chloro, fluoro or bromo; $C_{1-6}$alkyl; or two vicinal $R^6$ radicals may be taken together to form a bivalent radical of formula —CH=CH—CH=CH—;

f) $R^7$ is hydrogen.

Preferred compounds of the present invention are compound 50, 206, 31, 26, 27, 32, 33, 109, 39, 44, 41, compound A, E and F, a pharmaceutically acceptable acid or base addition salt thereof or a N-oxide form thereof.

Another group of preferred compounds are the compounds defined in claim 24, i.e. compounds 36, 46, 206, 31, 26, 33, 13, 39, 44, Compound A, E and F, a pharmaceutically acceptable acid or base addition salt thereof or a N-oxide form thereof.

The present invention also relates to a compound as claimed in claim 29, i.e. compounds A, B, C, D, E, F, G, H, I, a pharmaceutically acceptable acid or base addition salt thereof or a N-oxide form thereof.

The compounds of formula (I) can be prepared according to the methods described in WO 2004/011436, which is incorporated herein by reference.

In general, the compounds according to the invention can be prepared by a succession of steps, each of which is known to the skilled person.

In particular, the compounds according to formula (I) can be prepared by reacting an intermediate compound of formula (II) with an intermediate compound of formula (III) according to the following reaction scheme (1):

Scheme 1

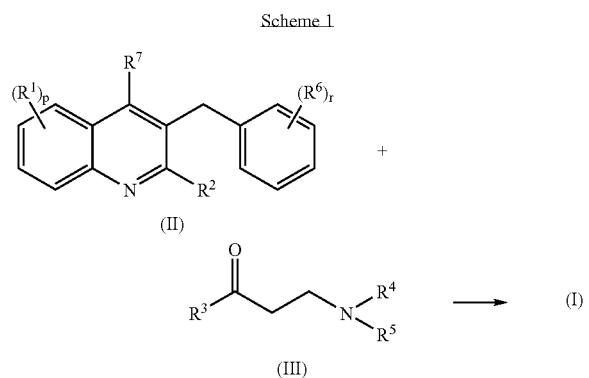

using BuLi in a mixture of diisopropyl amine and tetrahydrofuran, and wherein all variables are defined as in formula (I). Stirring may enhance the rate of the reaction. The reaction may conveniently be carried out at a temperature ranging between −20 and −70° C.

The starting materials and the intermediate compounds of formula (II) and (III) are compounds that are either commercially available or may be prepared according to conventional reaction procedures generally known in the art. For example, intermediate compounds of formula (II-a) may be prepared according to the following reaction scheme (2):

formylation followed by cyclization). The reaction may conveniently be carried out at a temperature ranging between room temperature and reflux temperature. In a next step (c) a specific $R^2$-group, wherein $R^2$ is for example an $C_{1-6}$alkyloxy or $C_{1-6}$alkylthio radical is introduced by reacting the intermediate compound obtained in step (b) with a compound H—X—$C_{1-6}$alkyl wherein X is S or O.

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC. Typically, compounds of formula (I) may be separated into their isomeric forms.

The intermediate compounds of formula (III) are compounds that are either commercially available or may be prepared according to conventional reaction procedures generally known in the art. For example, intermediate compounds of formula (III-a) in which $R^3$ is Ar substituted with s substituents $R^{10}$, wherein each $R^{10}$ is independently selected from the group of hydroxy, halo, cyano, nitro, amino, mono- or di($C_{1-6}$alkyl)amino, $C_{1-6}$alkyl, polyhalo$C_{1-6}$alkyl, $C_{1-6}$alkyloxy, polyhalo$C_{1-6}$alkyloxy, carboxyl, $C_{1-6}$alkyloxycarbonyl, aminocarbonyl, morpholinyl and mono- or di($C_{1-6}$alkyl)aminocarbonyl and s is an integer equal to zero, 1, 2 or 3, may be prepared according to the following reaction scheme (3):

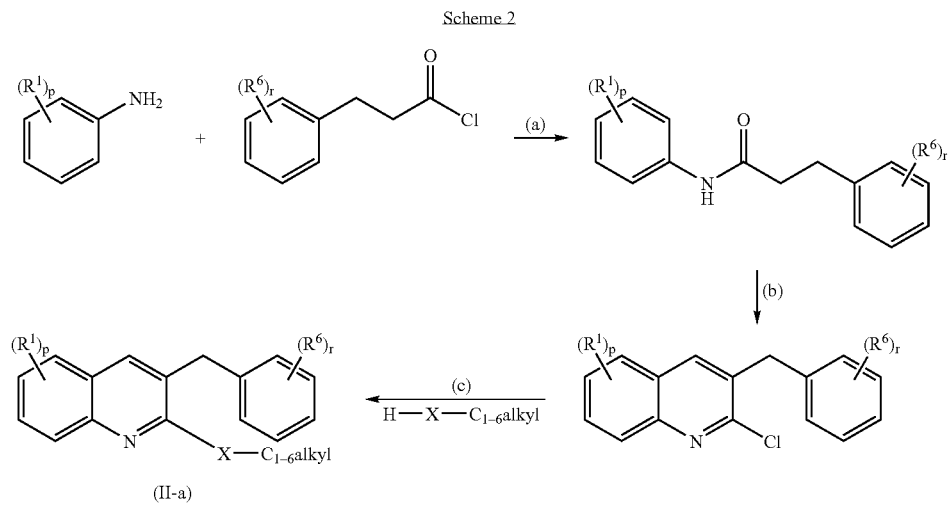

wherein all variables are defined as in formula (I). Reaction scheme (2) comprises step (a) in which an appropriately substituted aniline is reacted with an appropriate acylchloride such as 3-phenylpropionyl chloride, 3-fluorobenzenepropanoyl chloride or p-chlorobenzenepropanoyl chloride, in the presence of a suitable base, such as triethylamine and a suitable reaction-inert solvent, such as methylene chloride or ethylene dichloride. The reaction may conveniently be carried out at a temperature ranging between room temperature and reflux temperature. In a next step (b) the adduct obtained in step (a) is reacted with phosphoryl chloride ($POCl_3$) in the presence of N,N-dimethylformamide (Vilsmeier-Haack Scheme 3

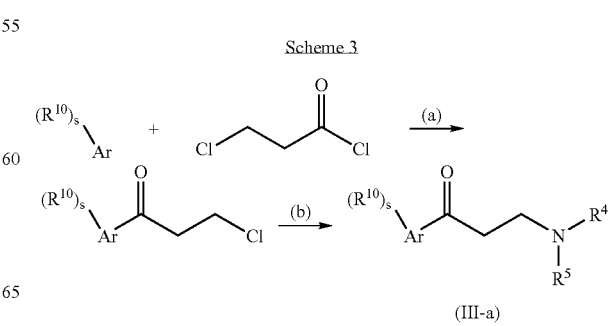

Reaction scheme (3) comprises step (a) in which an appropriately substituted Ar, in particular an appropriately substituted phenyl, is reacted by Friedel-Craft reaction with an appropriate acylchloride such as 3-chloropropionyl chloride, in the presence of a suitable Lewis acid, such as for example $AlCl_3$, $FeCl_3$, $SnCl_4$, $TiCl_4$ or $ZnCl_2$ and a suitable reaction-inert solvent, such as methylene chloride or ethylene dichloride. The reaction may conveniently be carried out at a temperature ranging between room temperature and reflux temperature. In a next step (b) an amino group ($—NR^4R^5$) is introduced by reacting the intermediate compound obtained in step (a) with $HNR^4R^5$.

In general, bacterial pathogens may be classified as either gram-positive or gram-negative pathogens. Antibiotic compounds with activity against both gram-positive and gram-negative pathogens are generally regarded as having a broad spectrum of activity. The compounds of the present invention are regarded as active against gram-positive and/or gram-negative bacterial pathogens. In particular, the present compounds are active against at least one gram-positive bacterium, preferably against several gram-positive bacteria, more preferably against one or more gram-positive bacteria and/or one or more gram-negative bacteria.

The present compounds have bactericidal or bacteriostatic activity.

Examples of gram-positive and gram-negative aerobic and anaerobic bacteria, include Staphylococci, for example *S. aureus*; Enterococci, for example *E. faecalis*; Streptococci, for example *S. pneumoniae, S. mutans, S. pyogenes*; Bacilli, for example *Bacillus subtilis; Listeria*, for example *Listeria monocytogenes; Haemophilus*, for example *H. influenza; Moraxella*, for example *M. catarrhalis; Pseudomonas*, for example *Pseudomonas aeruginosa*; and *Escherichia*, for example *E. coli*. Gram-positive pathogens, for example Staphylococci, Enterococci and Streptococci are particularly important because of the development of resistant strains which are both difficult to treat and difficult to eradicate from for example a hospital environment once established. Examples of such strains are methicillin resistant *Staphylococcus aureus* (MRSA), methicillin resistant coagulase negative staphylococci (MRCNS), penicillin resistant *Streptococcus pneumoniae* and multiple resistant *Enterococcus faecium*.

The compounds of the present invention also show activity against resistant bacterial strains.

The compounds of the present invention are especially active against *Staphylococcus aureus*, including resistant *Staphylococcus aureus* such as for example methicillin resistant *Staphylococcus aureus* (MRSA), and *Streptococcus pneumoniae*.

In particular, the compounds of the present invention are active on those bacteria of which the viability depends on proper functioning of F1F0 ATP synthase. Without being bound to any theory, it is taught that the activity of the present compounds lies in inhibition of the F1F0 ATP synthase, in particular the inhibition of the F0 complex of the F1F0 ATP synthase, more in particular the inhibition of subunit c of the F0 complex of the F1F0 ATP synthase, leading to killing of the bacteria by depletion of the cellular ATP levels of the bacteria.

Whenever used hereinbefore or hereinafter, that the compounds can treat a bacterial infection it is meant that the compounds can treat an infection with one or more bacterial strains.

Whenever used hereinbefore or hereinafter, that the bacterial infection is other than a Mycobacterial infection it is meant that the bacterial infection is other than an infection with one or more Mycobacterial strains.

The exact dosage and frequency of administration of the present compounds depends on the particular compound of formula (I) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention.

The compound of the present invention may be administered in a pharmaceutically acceptable form optionally in a pharmaceutically acceptable carrier. The compounds and compositions comprising the compounds can be administered by routes such as topically, locally or systemically. Systemic application includes any method of introducing the compound into the tissues of the body, e.g., intrathecal, epidural, intramuscular, transdermal, intravenous, intraperitoneal, subcutaneous, sublingual, rectal, and oral administration. The specific dosage of antibacterial to be administered, as well as the duration of treatment, may be adjusted as needed.

Bacterial infections which may be treated by the present compounds include, for example, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients.

Given the fact that the compounds of formula (I) are active against gram-positive and/or gram-negative bacteria, the present compounds may be combined with other antibacterial agents in order to effectively combat bacterial infections.

Therefore, the present invention also relates to a combination of (a) a compound of formula (I), and (b) one or more other antibacterial agents provided that the one or more other antibacterial agents are other than antimycobacterial agents.

The present invention also relates to a combination of (a) a compound of formula (I), and (b) one or more other antibacterial agents provided that the one or more other antibacterial agents are other than antimycobacterial agents, for use as a medicine.

A pharmaceutical composition comprising a pharmaceutically acceptable carrier and, as active ingredient, a therapeutically effective amount of (a) a compound of formula (I), and (b) one or more other antibacterial agents provided that the one or more other antibacterial agents are other than antimycobacterial agents, is also comprised by the present invention.

The present invention also relates to the use of a combination or pharmaceutical composition as defined above for the treatment of a bacterial infection, in particular a bacterial infection other than a Mycobacterial infection.

The present pharmaceutical composition may have various pharmaceutical forms for administration purposes. As appropriate compositions there may be cited all compositions usually employed for systemically administering drugs. To prepare the pharmaceutical compositions of this invention, an effective amount of the particular compounds, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral unit dosage forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight of the active ingredients, and, from 1 to 99.95% by weight, more preferably from 30 to 99.9 weight % of a pharmaceutically acceptable carrier, all percentages being based on the total composition.

The weight to weight ratio's of the compound of formula (I) and (b) the other antibacterial agent(s) when given as a combination may be determined by the person skilled in the art. Said ratio and the exact dosage and frequency of administration depends on the particular compound of formula (I) and the other antibacterial agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention.

The compounds of formula (I) and the one or more other antibacterial agents may be combined in a single preparation or they may be formulated in separate preparations so that they can be administered simultaneously, separately or sequentially. Thus, the present invention also relates to a product containing (a) a compound of formula (I), and (b) one or more other antibacterial agents provided that the one or more other antibacterial agents are other than antimycobacterial agents, as a combined preparation for simultaneous, separate or sequential use in the treatment of a bacterial infection.

The pharmaceutical composition may additionally contain various other ingredients known in the art, for example, a lubricant, stabilising agent, buffering agent, emulsifying agent, viscosity-regulating agent, surfactant, preservative, flavouring or colorant.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. The daily dosage of the compound according to the invention will, of course, vary with the compound employed, the mode of administration, the treatment desired and the bacterial disease indicated.

The other antibacterial agents which may be combined with the compounds of formula (I) are antibacterial agents known in the art. The other antibacterial agents comprise antibiotics of the β-lactam group such as natural penicillins, semisynthetic penicillins, natural cephalosporins, semisynthetic cephalosporins, cephamycins, 1-oxacephems, clavulanic acids, penems, carbapenems, nocardicins, monobactams; tetracyclines, anhydrotetracyclines, anthracyclines; aminoglycosides; nucleosides such as N-nucleosides, C-nucleosides, carbocyclic nucleosides, blasticidins; macrolides such as 12-membered ring macrolides, 14-membered ring macrolides, 16-membered ring macrolides; ansamycins; peptides such as bleomycins, gramicidins, polymyxins, bacitracins, large ring peptide antibiotics containing lactone linkages, actinomycins, amphomycin, capreomycin, distamycin, enduracidins, mikamycin, neocarzinostatin, stendomycin, viomycin, virginiamycin; cycloheximide; cycloserine; variotin; sarkomycin A; novobiocin; griseofulvin; chloramphenicol; mitomycins; fumagillin; monensins; pyrrolnitrin; fosfomycin; fusidic acid; D-(p-hydroxyphenyl)glycine; D-phenylglycine; enediynes.

Specific antibiotics which may be combined with the present compounds of formula (I) are for example benzylpenicillin (potassium, procaine, benzathine), phenoxymethylpenicillin (potassium), phenethicillin potassium, propicillin, carbenicillin (disodium, phenyl sodium, indanyl sodium), sulbenicillin, ticarcillin disodium, methicillin sodium, oxacillin sodium, cloxacillin sodium, dicloxacillin, flucloxacillin, ampicillin, mezlocillin, piperacillin sodium, amoxicillin, ciclacillin, hectacillin, sulbactam sodium, talampicillin hydrochloride, bacampicillin hydrochloride, pivmecillinam, cephalexin, cefaclor, cephaloglycin, cefadroxil, cephradine, cefroxadine, cephapirin sodium, cephalothin sodium, cephacetrile sodium, cefsulodin sodium, cephaloridine, cefatrizine, cefoperazone sodium, cefamandole, vefotiam hydrochloride, cefazolin sodium, ceftizoxime sodium, cefotaxime sodium, cefinenoxime hydrochloride, cefuroxime, ceftriaxone sodium, ceftazidime, cefoxitin, cefmetazole, cefotetan, latamoxef, clavulanic acid, imipenem, aztreonam, tetracycline, chlortetracycline hydrochloride, demethylchlortetracycline, oxytetracycline, methacycline, doxycycline, rolitetracycline, minocycline, daunorubicin hydrochloride, doxorubicin, aclarubicin, kanamycin sulfate, bekanamycin, tobramycin, gentamycin sulfate, dibekacin, amikacin, micronomicin, ribostamycin, neomycin sulfate, paromomycin sulfate, streptomycin sulfate, dihydrostreptomycin, destomycin A, hygromycin B, apramycin, sisomicin, netilmicin sulfate, spectinomycin hydrochloride, astromicin sulfate, validamycin, kasugamycin, polyoxin, blasticidin S, erythromycin, erythromycin estolate, oleandomycin phosphate, tracetyloleandomycin, kitasamycin, josamycin, spiramycin, tylosin, ivermectin, midecamycin, bleomycin sulfate, peplomycin sulfate, gramicidin S, polymyxin B, bacitracin, colistin sulfate, colistinmethanesulfonate sodium, enramycin, mikamycin, virginiamycin, capreomycin sulfate, viomycin, enviomycin, vancomycin, actinomycin D, neocarzinostatin, bestatin, pepstatin, monensin, lasalocid, salinomycin, amphotericin B, nystatin, natamycin, trichomycin, mithramycin, lincomycin, clindamycin, clindamycin palmitate hydrochloride, flavophospholipol, cycloserine, pecilocin, griseofulvin, chloramphenicol, chloramphenicol palmitate, mitomycin C, pyrrolnitrin, fosfomycin, fusidic acid, bicozamycin, tiamulin, siccanin.

Tables 1 to 4 list compounds of formula (I) according to the present invention.

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction.

In case "A" and "B" are stereoisomeric mixtures, they can be further separated whereby the respective first fractions isolated are designated "A1" respectively "B1" and the second as "A2" respectively "B2", without further reference to the actual stereochemical configuration. However, said "A1, A2" and "B1, B2" isomeric forms can be unambiguously characterized by a person skilled in the art, using art-known methods such as, for example, X-ray diffraction.

Whenever hereinabove or hereinafter, a compound is designated as "A" or "B" this means that the compound is a mixture of two enantiomers. Whenever hereinabove or hereinafter, a compound is designated as "A1", "A2", "B1" or "B2" this means that the compound is an enantiomer.

The relative configuration of the present compounds indicated by erythro and threo was determined by NMR, performed on a Bruker Avance 400 MHz (samples were dissolved in CDCl$_3$), by comparing the chemical shifts of a maximum of protons between the different stereoisomers or by 2D NOESY;

LCMS performed on a Applied Biosystems API100 Single quadrupole Mass Spectrometer. Samples were dissolved in a mixture of acetonitrile/methanol and injected in Flow Injection Analysis mode and analysed in positive electrospray using a 40V declustering potential. The designation of erythro/threo was based on the [MH+] ion peak corresponding to the loss of methanol (resulting from the fragmentation in the elctrospray source). When the ion is produced, it is bigger on spectrum of threo than on spectrum of erythro compound.

The present compounds are numbered in conformity with the compounds of WO 2004/011436 and can be prepared according to the methods described in WO 2004/011436. The Ex. Nr. in the below Tables refer to the Example numbers of WO 2004/011436 indicating according to which procedure the compounds can be prepared.

Additional compounds are indicated by way of letters.

Compound A, B and C were prepared according to the procedures described in WO 2004/011436. The scheme below indicates the synthesis pathway of compound A, B and C. The Example numbers A8, A9, B12 and B13 correspond to the procedures of WO 2004/011436.

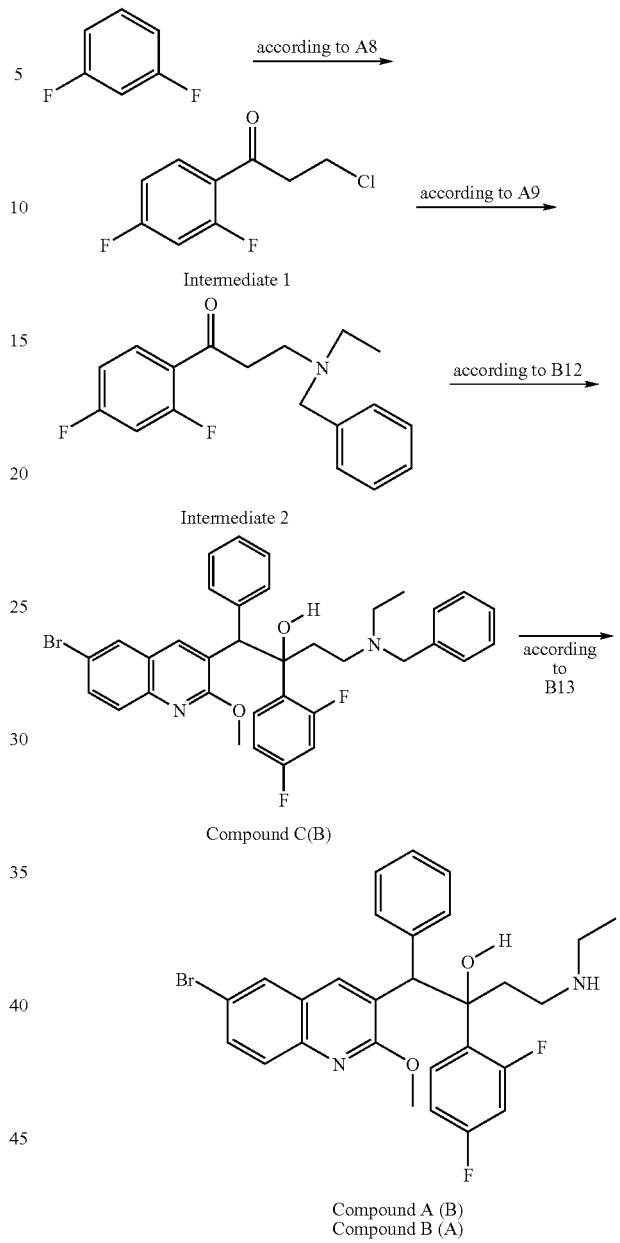

Present intermediate 1 was prepared in the same way as intermediate 12 of WO 2004/011436, i.e. according to Example A8 of WO 2004/011436, but starting from 1,3-difluorobenzene. Yield: 57% of present intermediate 1.

Present intermediate 2 was prepared in the same way as intermediate 14 of WO 2004/011436, i.e. according to Example A9 of WO 2004/011436, but starting from present intermediate 1 and reacting it with N-ethylbenzylamine. Yield: 88% of present intermediate 2.

Compound C was prepared as follows:

present intermediate 2 was reacted with intermediate compound 3 of WO 2004/011436 in the same way as described in Example B12 of WO 2004/011436. The residue (5.4 g) obtained according to the procedure of B12, which is a mixture of diastereoisomers, was purified by column chromatography over silica gel (eluent: CH$_2$Cl$_2$/Cyclohexane: 60/40). Two fractions were collected and the solvent was evaporated.

The second fraction was crystallized from diisopropylether yielding 0.83 g of compound C (diastereoisomer B) (yield: 13%).

Compounds A and B were prepared as follows:

The residue obtained in the synthesis of compound C was reacted with 1-chloroethyl chloroformate in the same way as described in Example B13 of WO 2004/011436. The residue (1.7 g) obtained according to the procedure of Example B13, which is mixture of diastereoisomers, was purified by column chromatography over silica gel (eluent: $CH_2Cl_2/CH_3OH/NH_4OH$; 98/2/0.1). Two fractions were collected and the solvent was evaporated. The fractions were crystallized separately from diisopropylether yielding 0.31 g of compound B (diastereoisomer A) (yield:27%) and 0.52 g of compound A (diastereoisomer B) (yield:45%).

Compound D was prepared according to the procedures described in WO 2004/011436. The scheme below indicates the synthesis pathway of compound D. The Example numbers A9, B12 and B13 correspond to the procedures of WO 2004/011436.

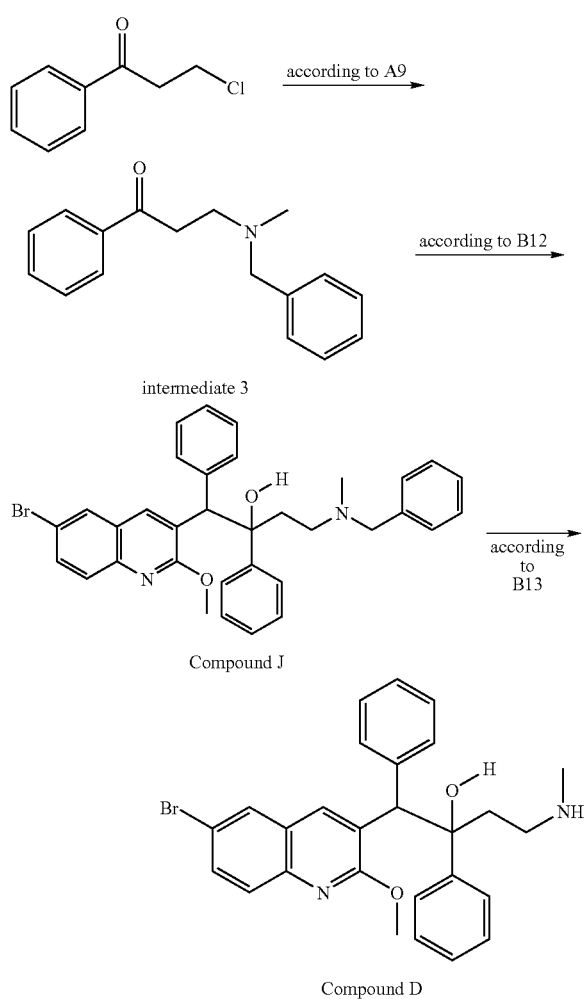

Present intermediate 3 was prepared in the same way as intermediate 14 of WO 2004/011436, i.e. according to Example A9 of WO 2004/011436, but starting from 3-chloropropiophenone. Yield: 98% of present intermediate 3.

Compound J was prepared as follows:

present intermediate 3 was reacted with intermediate compound 3 of WO 2004/011436 in the same way as described in Example B12 of WO 2004/011436. The obtained residue (4.9 g) was purified by column chromatography over silica gel (eluent: $CH_2Cl_2$). One fraction was collected and the solvent was evaporated. Yield: 1.43 g of compound J, which is a mixture of diastereoisomers.

Compound D was prepared as follows:

compound J was reacted with 1-chloroethyl formate in the same way as described in Example B13 of WO 2004/011436. The residue (1.2 g) obtained according to the procedure of Example B13 was purified by column chromatography over silica gel (eluent: $CH_2Cl_2/CH_3OH/NH_4OH$; 95/5/0.5). Two fractions were collected and the solvent was evaporated. The second fraction was crystallized from diisopropylether yielding 0.08 g of compound D (diastereoisomer B) (yield: 10%).

Compounds E and F were prepared by separating compound 4 (diastereoisomer B) of WO 2004/011436 into its enantiomers by the following procedure:

Final compound 4 of WO 2004/011436 (2.5 g) was separated into its enantiomers by column chromatography (eluent: hexane/ethanol 99.95/0.05; column: CHIRACEL OD). Two pure fractions were collected and their solvents were evaporated. Yield: 0.5 g of compound E (enantiomer B1) (mp. 180° C.) and 0.12 g of compound F (enantiomer B2) (mp. 175° C.).

Compound G was prepared as follows:

A mixture of compound 115 of WO 2004/011436 (prepared according to B15 of WO 2004/011436) (0.00028 mol), pyridine-3-boronic acid 1,3-propanediol cyclic ester (0.00055 mol), $Pd[P(Ph_3)]_4$ (0.00003 mol) and $Na_2CO_3$ 2M (0.0011 mol) in dimethoxyethane (4 ml) was stirred at 90° C. for 1.5 hours, then poured out into $H_2O$ and extracted with $CH_2Cl_2$. The organic layer was separated, dried ($MgSO_4$), filtered and the solvent was evaporated. The residue was purified by column chromatography over silica gel (eluent: $CH_2Cl_2/CH_3OH$ 95/5; 5 µm). The pure fractions were collected and the solvent was evaporated. Yield: 0.09 g of compound G (60%) (mp. 201° C.).

Compound H was prepared as follows:

A mixture of compound 15 of WO 2004/011436 (prepared according to B7 of WO 2004/011436) (0.0009 mol), 2-furanboronic acid (0.0018 mol), $Pd[P(Ph_3)]_4$ (0.00009 mol) and $Na_2CO_3$ 2M (0.0036 mol) in dimethoxyethane (10 ml) was stirred at 90° C. for 6 hours, then poured out into $H_2O$ and extracted with $CH_2Cl_2$. The organic layer was separated, dried ($MgSO_4$), filtered and the solvent was evaporated. The residue (0.57 g) was purified by column chromatography over silica gel (eluent: $CH_2Cl_2/CH_3OH/NH_4OH$ 99/1/0.1; 10 µm). The pure fractions were collected and the solvent was evaporated, yielding 0.23 g of residue. This fraction was crystallized from diisopropylether/acetonitrile. The precipitate was filtered off and dried. Yield: 0.071 g of compound H (15%) (mp. 215° C.).

Compound I was prepared according to the procedures described in WO 2004/011436. The scheme below indicates the synthesis pathway of compound I. The Example numbers A10 and B1 correspond to the procedures of WO 2004/011436.

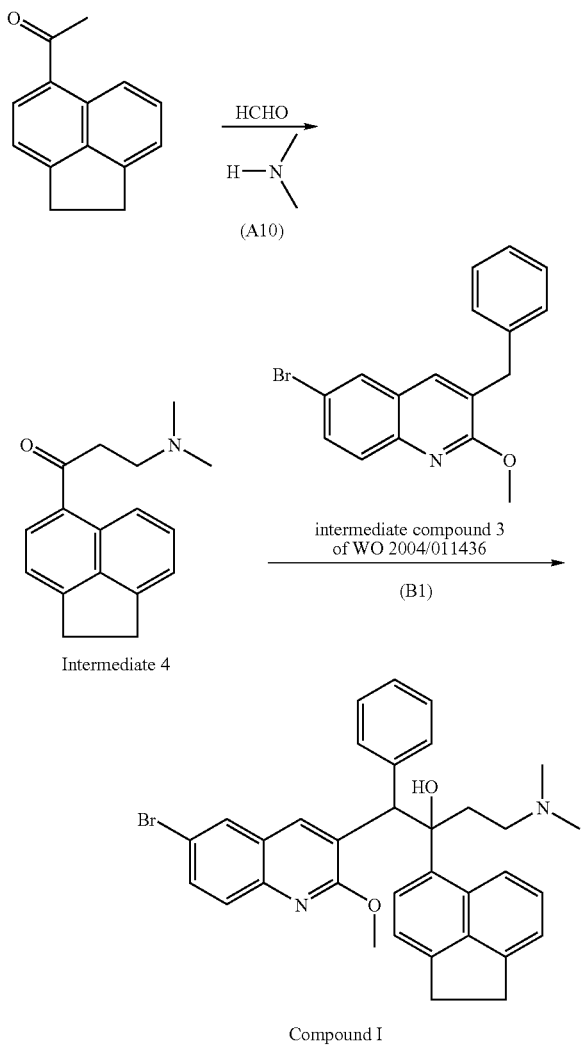

A mixture of commercially available 5-acetyl-1,2-dihydroacenaphtylene (0.0407 mol) and dimethylamine hydrochloride (0.0858 mol) in paraformaldehyde (37% in water, 4 ml), HCl/iPrOH (1 ml) and ethanol (100 ml) was stirred and refluxed for 48 hours. The solvent was evaporated. The residue was taken up in $H_2O$/HCl 3N/$CH_2Cl_2$. The aqueous layer was basified and extracted with $CH_2Cl_2$. The organic layer was separated, dried ($MgSO_4$), filtered, and the solvent was evaporated. The residue was purified by column chromatography over silica gel (eluent: $CH_2Cl_2$/$CH_3OH$/$NH_4OH$ 95/5/0.2; 15-40 μm). The pure fractions were collected and the solvent was evaporated.

Yield: 4.9 g of intermediate 4 (48%).

n-BuLi 1.6M (0.0102 mol) was added dropwise at −20° C. to a solution of diisopropylamine (0.0091 mol) in tetrahydrofuran (15 ml) under $N_2$ flow. The mixture was stirred at −20° C. for 20 minutes, then cooled to −70° C. A solution of intermediate compound 3 of WO 2004/011436 (0.0091 mol) in tetrahydrofuran (10 ml) was added dropwise. The mixture was stirred at −70° C. for 2 hours. A solution of present intermediate 4 (0.01 mol) in tetrahydrofuran (20 ml) was added dropwise. The mixture was stirred at −70° C. for 3 hours, poured out into ice water and extracted with EtOAc. The organic layer was separated, dried ($MgSO_4$), filtered, and the solvent was evaporated. The residue (6.5 g) was purified by column chromatography over silica gel (eluent: $CH_2Cl_2$/$CH_3OH$/$NH_4OH$ 99/1/0.2; 15-40 μm). Two fractions were collected and the solvent was evaporated. Yield: 0.96 g F1, 0.72 g F2. F1 was crystallized from diethyl ether. The precipitate was filtered off and dried. Yield: 0.87 g of compound I (17%).

TABLE 1

| Comp. nr. | Ex. nr. | $R^1$ | $R^2$ | $R^3$ | $R^6$ | Stereochemistry and melting points |
|---|---|---|---|---|---|---|
| 41 | B1 | H | $OCH_3$ | phenyl | H | (B); 160° C. |
| 206 | B7 | Br | $OCH_3$ | 1-naphthyl | F | (B) mixture of 2 enantiomers is erythro/syn; 213° C. |
| 31 | B1 | Cl | $OCH_3$ | phenyl | H | (B) mixture of 2 enantiomers is erythro/syn; 181° C. |

TABLE 1-continued

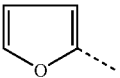

| Comp. nr. | Ex. nr. | R¹ | R² | R³ | R⁶ | Stereochemistry and melting points |
|---|---|---|---|---|---|---|
| 26 | B1 | phenyl | OCH₃ | phenyl | H | (A) mixture of 2 enantiomers is threo/anti; 174° C. |
| 27 | B1 | phenyl | OCH₃ | phenyl | H | (B); 192° C. |
| 32 | B1 | Br | SCH₃ | phenyl | H | (A); 208° C. |
| 33 | B1 | Br | SCH₃ | phenyl | H | (B) mixture of 2 enantiomers is erythro/syn; 196° C. |
| 109 | B9 | Br | OCH₃ | 3-fluorophenyl | H | (A2); 156° C. |
| 39 | B9 | Br | OCH₃ | 3-fluorophenyl | H | (B) mixture of 2 enantiomers is erythro/syn; 207° C. |
| 36 | B1 | Br | OCH₃ | phenyl | Cl | (A) mixture of 2 enantiomers is erythro/syn; 197° C. |
| 14 | B7 | Br | OCH₃ | 1-naphthyl | H | (A); 210° C. |
| 15 | B7 | Br | OCH₃ | 1-naphthyl | H | (B); 244° C. |
| 46 | B7 | Br | OCH₃ | 2-naphthyl | H | (B) mixture of 2 enantiomers is erythro/syn; 162° C. |
| 4 | B1 | Br | OCH₃ | phenyl | H | (B); 190° C. |
| 174 | B9 | 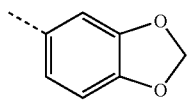 | OCH₃ | 3-fluorophenyl | H | (A); 159° C. |
| 24 | B1 | Br | OCH₃ | 3-thienyl | H | (A); 162° C. |
| 5 | B2 | Br | OCH₂CH₃ | phenyl | H | (A); 162° C. |
| 38 | B9 | Br | OCH₃ | 3-fluorophenyl | H | (A); 198° C. |
| 69 | B1 | Br | OCH₃ | 2-fluorophenyl | H | (A); oil |
| 70 | B1 | Br | OCH₃ | 2-fluorophenyl | H | (B); oil |
| 16 | B1 | Br | OCH₃ | 4-chlorophenyl | H | (A); 200° C. |
| 17 | B1 | Br | OCH₃ | 4-chlorophenyl | H | (B); 190° C. |
| 67 | B8 | Br | OCH₃ | 2,5-difluorophenyl | H | (A); 60° C. |
| 116 | B15 | Br | OCH₃ | 3,5-difluorophenyl | H | (B); 224° C. |
| 159 | B8 | Br | OCH₃ | 2,5-difluorophenyl | H | (A1); 208° C. |
| 160 | B8 | Br | OCH₃ | 2,5-difluorophenyl | H | (A2); 167° C. |
| 113 | B14 | Br | OCH₃ | 2,3-difluorophenyl | H | (A); 128° C. |
| 196 | B15 | Br | OCH₃ | 3,4-difluorophenyl | H | (B); 184° C. |
| 76 | B1 | Br | OCH₃ | 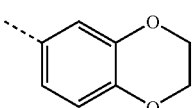 | H | (B); 130° C. |
| 84 | B1 | phenyl | OCH₃ | 1-naphthyl | H | (A); 248° C. |
| 45 | B7 | Br | OCH₃ | 2-naphthyl | H | (A); 262° C. |
| 77 | B1 | Br | OCH₃ | 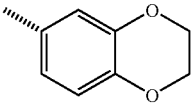 | H | (A); 202° C. |
| 78 | B1 | Br | OCH₃ | 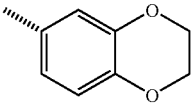 | H | (B); 202° C. |

TABLE 1-continued

| Comp. nr. | Ex. nr. | R¹ | R² | R³ | R⁶ | Stereochemistry and melting points |
|---|---|---|---|---|---|---|
| 165 | B9 | Br | 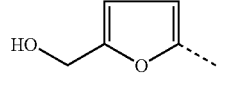 | 3-fluorophenyl | H | (B); oil |
| 72 | B1 | Br | OCH₃ | 1-naphthyl | CH₃ | (B); 178° C. |
| 212 | B7 | 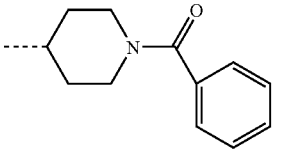 | OCH₃ | 1-naphthyl | H | (B); 220° C. |
| 163 | B7 | Br | OCH₃ | 6-methoxy-2-naphthyl | H | (B); 206° C. |
| 73 | B1 | Br | OCH₃ | 1-naphthyl | Cl | (B); 174° C. |
| 201 | B1 | Br | OCH₃ | 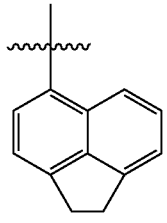 | H | (A); 214° C. |
| 30 | B1 | Cl | OCH₃ | phenyl | H | (A); 170° C. |
| 21 | B1 | Br | OCH₃ | 2-thienyl | H | (B); 176° C. |
| 25 | B1 | Br | OCH₃ | 3-thienyl | H | (B); 160° C. |
| 20 | B1 | Br | OCH₃ | 2-thienyl | H | (A); 96° C. |
| 6 | B2 | Br | OCH₂CH₃ | phenyl | H | (B); 74° C. |
| 108 | B9 | Br | OCH₃ | 3-fluorophenyl | H | (A1); 160° C. |
| 37 | B1 | Br | OCH₃ | phenyl | Cl | (B); 221° C. |
| 13 | B7 | Br | OCH₃ | 1-naphthyl | H | (A1) enantiomer is threo/anti; (1S,2R) 120° C. |
| 130 | B7 | Br | OCH₃ | 5-bromo-2-naphthyl | H | (B); 220° C. |
| G | | 3-pyridyl | OCH₃ | 3,5-difluorophenyl | H | (A) mixture of 2 enantiomers is threo/anti; 201° C. |
| H | | 2-furanyl | OCH₃ | 1-naphthyl | H | (B) mixture of 2 enantiomers is erythro/syn; 215° C. |
| I | | | Br | OCH₃ | H | (A) mixture of 2 enantiomers is threo/anti; >260° C. |
| F | B1 | Br | OCH₃ | phenyl | H | (B2) enantiomer is erythro/syn; 175° C. |
| E | B1 | Br | OCH₃ | phenyl | H | (B1) enantiomer is erythro/syn; 180° C. |

TABLE 2

| Comp. nr. | Ex. nr. | $R^1$ | $R^2$ | $R^3$ | $R^4$ | $R^5$ | Phys. data (salt/melting points) and stereochemistry |
|---|---|---|---|---|---|---|---|
| 44 | B4 | Br | $OCH_3$ | phenyl | H | H | (A) mixture of 2 enantiomers is threo/anti; 190° C. |
| 19 | B1 | Br | $OCH_3$ | phenyl | $CH_2CH_3$ | $CH_2CH_3$ | .ethanedioate (2:3), (B); 150° C. |
| 18 | B1 | Br | $OCH_3$ | phenyl | $CH_2CH_3$ | $CH_2CH_3$ | .ethanedioate (2:3); (A); 230° C. |

TABLE 3

| Comp nr. | Ex nr. | $R^3$ | L | Stereochemistry and melting points |
|---|---|---|---|---|
| 50 | B1 | phenyl | 1-imidazolyl | (B); 230° C. |
| 137 | B7 | 2-naphthyl | 4-methylpyrazinyl | (B); 232° C. |
| 154 | B7 | 6-bromo-2-naphthyl | 4-methylpiperazinyl | (B); 254° C. |
| 49 | B1 | phenyl | 1-imidazolyl | (A); 216° C. |
| 136 | B7 | 2-naphthyl | 4-methylpyrazinyl | (A); 188° C. |
| 48 | B1 | phenyl | 1-piperidinyl | (B); 210° C. |
| 55 | B1 | phenyl | thiomorpholinyl | (A); oil |
| 171 | B7 | 2-naplithyl | 1-pyrrolidinyl | (B); 218° C. |
| 129 | B1 | 2-naphthyl | 1-piperidinyl | (B); 212° C. |
| 149 | B7 | 1-naphthyl | 4-methylpyrazinyl | (B); 232° C. |
| 166 | B7 | 6-bromo-2-naphthyl | 1-piperidinyl | (B); 218° C. |
| 151 | B7 | 3-bromo-1-naphthyl | 4-methylpiperazinyl | (A); 178° C. |
| 53 | B1 | phenyl | 1-(1,2,4-triazolyl) | (A); 180° C. |
| 47 | B1 | phenyl | 1-piperidinyl | (A); 190° C. |
| 51 | B1 | phenyl | 1-(4-methyl)piperazinyl | (A); 150° C. |
| 170 | B7 | 2-naphthyl | 1-pyrrolidinyl | (A); 238° C. |
| 128 | B1 | 2-naphthyl | 1-piperidinyl | (A); 254° C. |
| 145 | B7 | 1-naphthyl | 1-piperidinyl | (A); 2i2° C. |
| 139 | B7 | 2-naphthyl | morpholinyl | (A); 258° C. |
| 140 | B7 | 2-naphthyl | morpholinyl | (B); 214° C. |
| 155 | B7 | 6-bromo-2-naphthyl | 1-piperidinyl | (A); 224° C. |
| A | B13 | 2,4-difluorophenyl | $NH(CH_2CH_3)$ | (B) mixture of 2 enantiomers is erythro/syn; 171° C. |
| B | B13 | 2,4-difluorophenyl | $NH(CH_2CH_3)$ | (A) mixture of 2 enantiomers is threo/anti |
| C | B12 | 2,4-difluorophenyl | $N(CH_2CH_3)(CH_2phenyl)$ | (B) mixture of 2 enantiomers is erythro/syn |
| D | B13 | phenyl | $NH(CH_3)$ | (B) mixture of 2 enantiomers is erythro/sun; 197° C. |

TABLE 3-continued

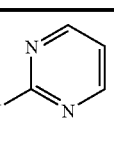

| Comp nr. | Ex nr. | R³ | L | Stereochemistry and melting points |
|---|---|---|---|---|
| 209 | B7 | 2-naphthyl |  | (B); 198° C. |
| 58 | B6 | phenyl |  | (A); 208° C. |
| 11 | B6 | phenyl | | (B); 208° C. |

TABLE 4

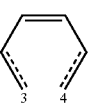

| Comp nr. | Ex. nr. | R¹ a | b | c | d | R³ | R⁶ | Sterechemistry and melting points |
|---|---|---|---|---|---|---|---|---|
| 215 | B9 | H | Br | $CH_3$ | H | 3-fluorophenyl | H | (A); 197° C. |
| 226 | B7 | H | Br | $CH_3$ | H | 1-naphthyl | H | (B); 208° C. |
| 229 | B7 | H | $CH_3$ | $CH_3$ | H | 1-naphthyl | H | (A); 238° C. |
| 227 | B15 | H | Br | $CH_3$ | H | 3,5-difluorophenyl | H | (A); 195° C. |
| 223 | B7 | H | Br | H | H | 1-naphthyl | 3,4 | (B); 205° C. |

Analytical Methods

The mass of some compounds was recorded with LCMS (liquid chromatography mass spectrometry). The method used is described below. The data are gathered in Table 5 below.

LCMS-Method

LCMS analysis was carried out (electrospray ionization in positive mode, scanning mode from 100 to 900 amu) on a Kromasil C18 column (Interchim, Montluçon, FR; 5 μm, 4.6×150 mm) with a flow rate of 1 ml/minute. Two mobile phases (mobile phase A: 30% 6.5 mM ammonium acetate+ 40% acetonitrile+30% formic acid (2 ml/l); mobile phase B: 100% acetonitrile) were employed to run a gradient condition from 100% A for 1 minute to 100% B in 4 minutes, 100% B for 5 minutes to 100% A in 3 minutes, and reequilibrate with 100% A for 2 minutes.

TABLE 5

| Compound No | LCMS parent peak (MH$^+$) |
|---|---|
| A | 541 |
| B | 541 |
| C | 631 |

PHARMACOLOGICAL EXAMPLES

Preparation of Bacterial Suspensions for Susceptibility Testing

The bacteria used in this study were grown overnight in flasks containing 100 ml Mueller-Hinton Broth (Becton Dickinson—cat. no. 275730) in sterile de-ionized water, with shaking, at 37° C. Stocks (0.5 ml/tube) were stored at −70° C. until use. Bacteria titrations were performed in microtiter plates to detect the TCID$_{50}$, in which the TCID50 represents the dilution that gives rise to bacterial growth in 50% of inoculated cultures.

In general, an inoculum level of approximately 100 TCID$_{50}$ was used for susceptibility testing.

Anti Bacterial Susceptibility Testing: IC$_{90}$ Determination

Microtitre Plate Assay

Flat-bottom, sterile 96-well plastic microtiter plates were filled with 180 µl of sterile deionized water, supplemented with 0.25% BSA. Subsequently, stock solutions (7.8× final test concentration) of compounds were added in 45 µl volumes in column 2. Serial five-fold dilutions (45 µl in 180 µl) were made directly in the microtiter plates from column 2 to reach column 11. Untreated control samples with (column 1) and without (column 12) inoculum were included in each microtiter plate. Depending on the bacteria type, approximately 10 to 60 CFU per well of bacteria inoculum (100 TCID50), in a volume of 100 µl in 2.8× Mueller-Hinton broth medium, was added to the rows A to H, except column 12. The same volume of broth medium without inoculum was added to column 12 in row A to H. The cultures were incubated at 37° C. for 24 hours under a normal atmosphere (incubator with open air valve and continuous ventilation). At the end of incubation, one day after inoculation, the bacterial growth was quantitated fluorometrically. Therefore resazurin (0.6 mg/ml) was added in a volume of 20 µl to all wells 3 hours after inoculation, and the plates were re-incubated overnight. A change in colour from blue to pink indicated the growth of bacteria. The fluorescence was read in a computer-controlled fluorometer (Cytofluor Biosearch) at an excitation wavelength of 530 nm and an emission wavelength of 590 nm. The % growth inhibition achieved by the compounds was calculated according to standard methods. The IC$_{90}$ (expressed in µg/ml) was defined as the 90% inhibitory concentration for bacterial growth. The results are shown in Table 6.

Agar Dilution Method.

MIC$_{99}$ values (the minimal concentration for obtaining 99% inhibition of bacterial growth) can be determined by performing the standard Agar dilution method according to NCCLS standards* wherein the media used includes Mueller-Hinton agar.

* Clinical laboratory standard institute. 2005. Methods for dilution Antimicrobial susceptibility tests for bacteria that grows Aerobically: approved standard-sixth edition Time Kill Assays Bactericidal or bacteriostatic activity of the compounds may be determined in a time kill assay using the broth microdilution method *. In a time kill assay on *Staphylococcus aureus* and methicillin resistant *S. aureus* (MRSA), the starting inoculum of *S. aurues* and MRSA is 10$^6$ CFU/ml in Muller Hinton broth. The antibacterial compounds are used at the concentration of 0.1 to 10 times the MIC (i.e. IC$_{90}$ as determined in microtitre plate assay). Wells receiving no antibacterial agent constitute the culture growth control. The plates containing the microorganism and the test compounds are incubated at 37° C. After 0, 4, 24, and 48 hrs of incubation samples are removed for determination of viable counts by serial dilution (10$^{-1}$ to 10$^{-6}$) in sterile PBS and plating (200 µl) on Mueller Hinton agar. The plates are incubated at 37° C. for 24 hrs and the number of colonies are determined. Killing curves can be constructed by plotting the log$_{10}$ CFU per ml versus time. A bactericidal effect is commonly defined as 3-log$_{10}$ decrease in number of CFU per ml as compared to untreated inoculum. The potential carryover effect of the drugs is removed by serial dilutions and counting the colonies at highest dilution used for plating.

* Zurenko, G. E. et al. In vitro activities of U-100592 and U-100766, novel oxazolidinone antibacterial agents. *Antimicrob. Agents Chemother.* 40, 839-845 (1996).

Determination of Cellular ATP Levels

In order to analyse the change in the total cellular ATP concentration (using ATP bioluminescence Kit, Roche), assays are carried out by growing a culture of *S. aureus* (ATCC29213) stock in 100 ml Mueller Hinton flasks and incubate in a shaker-incubator for 24 hrs at 37° C. (300 rpm). Measure OD$_{405}$ nm and calculate the CFU/ml. Dilute the cultures to 1×10$^6$ CFU/ml (final concentration for ATP measurement: 1×10$^5$ CFU/100 µl per well) and add test compound at 0.1 to 10 times the MIC (i.e. IC$_{90}$ as determined in microtitre plate assay). Incubate these tubes for 0, 30 and 60 minutes at 300 rpm and 37° C. Use 0.6 ml bacterial suspension from the snap-cap tubes and add to a new 2 ml eppendorf tubes. Add 0.6 ml cell lysis reagent (Roche kit), vortex at max speed and incubate for 5 minutes at room temperature. Cool on ice. Let the luminometer warm up to 30° C. (Luminoskan Ascent Labsystems with injector). Fill one column (=6 wells) with 100 µl of the same sample. Add 100 µl Luciferase reagent to each well by using the injector system. Measure the luminescence for 1 sec.

TABLE 6

IC$_{90}$ values (μg/ml) determined according to the Microtitre plate assay.

| Comp. No. | BSU 43639 | ECO 25922 | EFA 14506 | EFA 29212 | LMO 49594 | PAE 27853 | SMU 33402 | SPN 6305 | SPY 8668 | STA 43300 | STA 25923 | STA 29213 | STA RMETH |
|---|---|---|---|---|---|---|---|---|---|---|---|---|---|
| A | | | | | | | 10.8 | 1.1 | 10.8 | | 10.8 | 12.1 | |
| 50 | 10.5 | | | 10.5 | 23.6 | | 21.0 | | 26.5 | | | 26.5 | 10.5 |
| 41 | | | | | 17.0 | | | | | | | | |
| F | | | | | | | 22.6 | 25.3 | 22.6 | | | | |
| 206 | | | | | | | | 12.8 | | | | | |
| 31 | 10.3 | | | 4.6 | 4.1 | 10.3 | 10.3 | 5.2 | 1.8 | 11.6 | | | |
| 44 | 7.6 | | | | | | | | | | 7.6 | | |
| 26 | 10.0 | | | 4.5 | 4.5 | 2.0 | 11.3 | 5.6 | 2.5 | 11.3 | 8.9 | | |
| 27 | 10.0 | | | | | | | 12.6 | | | | | |
| E | 12.7 | | | 11.3 | 7.1 | 10.1 | 10.1 | 5.7 | 5.1 | 12.7 | | | |
| 32 | | 11.7 | | 4.6 | 4.6 | 10.4 | 4.6 | 13.1 | 4.6 | 13.1 | 9.3 | | 13.1 |
| 33 | 10.4 | | 11.7 | 4.6 | 2.3 | 11.7 | 10.4 | 5.9 | 2.6 | 5.9 | 13.1 | | |
| 109 | | | | 11.7 | 9.3 | 11.7 | | 13.1 | 13.1 | 13.1 | 10.4 | | |
| 39 | | | | 10.4 | 4.7 | 10.4 | 11.7 | 5.9 | 1.9 | 13.1 | 10.4 | | |
| 137 | | | | | | 21.2 | | 23.8 | | | 8.4 | | 21.2 |
| 36 | 24.1 | | | 4.8 | 5.4 | 4.8 | 3.8 | 2.7 | 0.4 | 4.8 | | | |
| 14 | 11.1 | | 9.9 | 5.0 | 2.5 | 5.0 | 12.4 | 6.2 | 2.8 | 5.6 | 9.9 | | 14.0 |
| 15 | 24.8 | | 24.8 | 5.0 | 2.5 | 12.4 | 12.4 | 6.2 | 2.2 | 5.0 | | | |
| 46 | | | | 5.0 | 2.8 | 5.0 | 5.6 | 2.8 | 0.6 | 5.6 | | | |
| 154 | 10.9 | | | 27.4 | 27.4 | | | | 27.4 | | 13.8 | | 24.5 |
| 4 | | | | | | | | 12.7 | | | | | |
| 174 | | | | | 10.2 | | | | | | | | |
| 175 | | | | | 10.2 | | | 12.8 | | | | | |
| 24 | | | | | | | | 10.2 | | | | | |
| 5 | | | | | | 10.4 | | | | | | | |
| 38 | | | | | 10.4 | | | | | | | | |
| 69 | | | | | 10.4 | 10.4 | | 13.1 | | | | | |
| 70 | | | | | 10.4 | | | 13.1 | | | | | |
| 49 | | | | | 10.5 | | 10.5 | 13.3 | 10.5 | | 5.9 | | 11.8 |
| 136 | 10.6 | | | 10.6 | 10.6 | | | | | | | | |
| 19 | | | | | | | | 13.4 | | | | | |
| 215 | | | | | 10.7 | | | | | | | | |
| G | 13.6 | | | 10.8 | 10.8 | | | | | | | | |
| 16 | | | | | | 13.6 | | | | | | | |
| 17 | | | | | 10.8 | | | 0.5 | | | | | |
| 67 | | | | | 10.8 | | | 13.6 | | | | | |
| 116 | | | | | 10.8 | | | | | | | | |
| 110 | | | | | 10.8 | | | 13.6 | | | | | |
| 111 | | | | | 10.8 | | | | | | | | |
| 113 | | | | | 10.8 | | | 13.6 | | | | | |
| 196 | | | | | | | 10.8 | | | | | | |
| B | | | | | | | | | | | 8.6 | | |
| H | | | | | 13.6 | | | 13.6 | | | | | |
| 48 | | | | | 10.9 | 10.9 | 10.9 | 13.7 | 13.7 | | | | |
| 76 | | | | | 11.0 | 11.0 | | | | | | | |
| 84 | | | | | 11.0 | | 11.0 | 7.0 | 11.0 | | | | |
| 45 | 11.1 | | 12.4 | | | | | | | | | | |
| 77 | | | | | | 11.2 | | 14.2 | | | | | |
| 78 | | | | | | | 11.2 | 11.2 | 11.2 | | | | |
| 55 | | | | | | | | 0.6 | | | | | |
| 165 | | | | | | | 14.3 | 14.3 | 11.3 | | | | |
| 72 | | | | | | | 9.0 | 14.3 | 11.4 | | | | |
| 226 | | | | | | | | 14.3 | | | | | |
| 212 | 11.4 | | | | | | | | | | | | |
| 171 | | | | | | | | | | | 11.6 | | |
| 163 | | | | | | | | 14.7 | | | | | |
| 73 | | | | | | | 11.8 | 14.8 | | | | | |
| 129 | | | | | | | 11.9 | 15.0 | 11.9 | | | | |
| 149 | | | | | 12.2 | | | | | | | | |
| 201 | 12.3 | | | 12.3 | 12.3 | 12.3 | | | | | | | |
| C | | | | | | | | 15.9 | | | | | |
| 18 | | | | 13.3 | 13.3 | | | 0.7 | | | | | |
| 166 | | | | | | | | 16.9 | | | | | |
| 151 | | 15.4 | | | | | | | | | | | 15.4 |
| 30 | | | | 10.3 | 10.3 | 9.2 | 10.3 | 5.2 | 10.3 | | | | |
| D | | | | | | | | 4.9 | | | | | |
| 229 | | | | | | | 22.5 | 5.0 | | | | | |
| 21 | | | | 11.5 | 4.6 | | 11.5 | 12.8 | | 12.8 | | | |
| 25 | | | | 11.5 | 11.5 | | 11.5 | 12.8 | 4.1 | 12.8 | | | |
| 20 | | | | | | | | 2.6 | | | | | |
| 6 | | | | 11.6 | 11.6 | 11.6 | 4.6 | 13.0 | 4.6 | | | | |
| 108 | | | | | | | | 13.1 | | | | | |

TABLE 6-continued

IC90 values (μg/ml) determined according to the Microtitre plate assay.

| Comp. No. | BSU 43639 | ECO 25922 | EFA 14506 | EFA 29212 | LMO 49594 | PAE 27853 | SMU 33402 | SPN 6305 | SPY 8668 | STA 43300 | STA 25923 | STA 29213 | STA RMETH |
|---|---|---|---|---|---|---|---|---|---|---|---|---|---|
| 53 | | | | | | | | 5.9 | | | | | |
| 37 | | | | | | | | 12.1 | | | | | |
| 47 | | | | | | | | 6.9 | | | | | |
| 227 | | | | | | | | 5.0 | | | | | |
| 13 | 11.1 | | 11.1 | 8.8 | 11.1 | 2.2 | 3.5 | 2.8 | 8.8 | 11.1 | 11.1 | | |
| 51 | 28.1 | | | 25.0 | 25.0 | | | 5.6 | | | | | |
| I | | | | | | | | 11.6 | | | | | |
| 170 | | | | | | | | 26.0 | | | | | |
| 128 | | | | | | 9.4 | | | | | | | |
| 145 | | | 23.7 | | | | | 9.4 | | | | | |
| 139 | | | | | | | 18.9 | 26.7 | | | | | |
| 140 | | | | | | | | 9.5 | | | | | |
| 223 | | | | | | | | 5.4 | 13.6 | 5.4 | | | |
| 130 | | | | | | | | 10.1 | | | | | |
| 155 | | | 26.9 | | | | | | | | | | |
| 209 | | | | | | | | 15.1 | | | | | |
| 58 | | | | | | | | 5.9 | | 8.3 | | | |
| 11 | | | | | 11.7 | | | 10.4 | | 11.7 | | | |

BSU 3639 means *Bacillus subtilis* (ATCC43639); ECO 25922 means *Escherichia coli* (ATCC25922); EFA 14506 means *Enterococcus faecalis* (ATCC14506); EFA 29212 means *Enterococcus faecalis* (ATCC29212); LMO 49594 means *Listeria monocytogenes* (ATCC49594); PAE 27853 means *Pseudomonas aeruginosa* (ATCC27853); SMU 33402 means *Streptococcus mutans* (ATCC33402); SPN 6305 means *Streptococcus pneumoniae* (ATCC6305); SPY 8668 means *Streptococcus pyogenes* (ATCC8668); STA 43300 means *Staphylococcus aureus* (ATCC43300); STA 25923 means *Staphylococcus aureus* (ATCC25923); STA 29213 means *Staphylococcus aureus* (ATCC29213); STA RMETH means methicilline resistant *Staphylococcus aureus* (MRSA) (a clinical isolate from the University of Antwerp). ATCC means American type tissue culture.

The invention claimed is:

1. A method for the treatment of a person suffering from a bacterial infection which comprises administering to said patient a therapeutically effective amount of a compound of formula

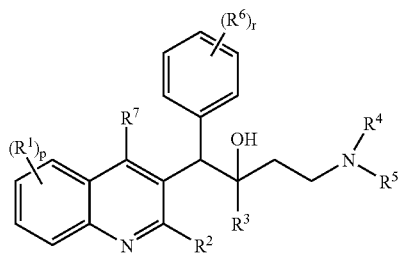

(I)

a pharmaceutically acceptable acid or base addition salt thereof, a stereochemically isomeric form thereof or a N-oxide form thereof, wherein $R^1$ is hydrogen, halo, polyhalo$C_{1-6}$alkyl, $C_{1-6}$alkyl, Ar or Het;

p is an integer equal to 1 or 2;

$R^2$ is $C_{1-6}$alkyloxy, $C_{1-6}$alkyloxy$C_{1-6}$alkyloxy or $C_{1-6}$alkylthio;

$R^3$ is Ar, Het or Het$^1$;

$R^4$ and $R^5$ each independently are hydrogen, $C_{1-6}$alkyl or benzyl; or $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, each of said rings may optionally be substituted with $C_{1-6}$alkyl, halo, polyhalo$C_{1-6}$alkyl, hydroxy, hydroxy$C_{1-6}$alkyl, $C_{1-6}$alkyloxy, amino, mono- or di($C_{1-6}$alkyl)amino, $C_{1-6}$alkylthio, $C_{1-6}$alkyloxy$C_{1-6}$alkyl, $C_{1-6}$alkylthio$C_{1-6}$alkyl or pyrimidinyl;

$R^6$ is hydrogen, halo, polyhalo$C_{1-6}$alkyl, $C_{1-6}$alkyl, $C_{1-6}$alkyloxy, $C_{1-6}$alkylthio; or two vicinal $R^6$ radicals may be taken together to form a bivalent radical of formula —CH=CH—CH=CH—;

r is an integer equal to 1 or 2;

$R^7$ is hydrogen, $C_{1-6}$alkyl, Ar, Het or Het$^1$;

Ar is a homocycle selected from the group of phenyl, naphthyl, acenaphthyl, tetrahydronaphthyl, each homocycle may optionally be substituted with 1, 2 or 3 substituents, each substituent independently selected from the group of hydroxy, halo, cyano, nitro, amino, mono- or di($C_{1-6}$alkyl)amino, $C_{1-6}$alkyl, polyhalo$C_{1-6}$alkyl, hydroxy$C_{1-6}$alkyl, $C_{1-6}$alkyloxy, polyhalo$C_{1-6}$alkyloxy, $C_{1-6}$alkyloxy$C_{1-6}$alkyl, carboxyl, $C_{1-6}$alkyloxycarbonyl, aminocarbonyl, morpholinyl and mono- or di($C_{1-6}$alkyl)aminocarbonyl;

Het is a monocyclic heterocycle selected from the group of N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; each monocyclic heterocycle may optionally be substituted with 1, 2 or 3 substituents, each substituent independently selected from the group of halo, hydroxy, $C_{1-6}$alkyl, polyhalo$C_{1-6}$alkyl, hydroxy$C_{1-6}$alkyl, $C_{1-6}$alkyloxy, $C_{1-6}$alkyloxy$C_{1-6}$alkyl or Ar—C(=O)—;

Het¹ is a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each bicyclic heterocycle may optionally be substituted with 1, 2 or 3 substituents, each substituent independently selected from the group of halo, hydroxy, $C_{1-6}$alkyl, polyhalo$C_{1-6}$ alkyl, hydroxy$C_{1-6}$alkyl, $C_{1-6}$alkyloxy, $C_{1-6}$alkyloxy$C_{1-6}$alkyl or Ar—C(=O)—;

provided that the bacterial infection is other than a Mycobacterial infection; and provided that the compound is other than (αS, βR)-6-bromo-α-[2-(dimethylamino)ethyl]-2-methoxy-α-1-naphthalenyl-β-phenyl-3-quinolineethanol, a pharmaceutically acceptable acid or base addition salt thereof or a N-oxide form thereof.

2. The method according to claim 1 wherein the compound of formula (I) is a compound having the following formula

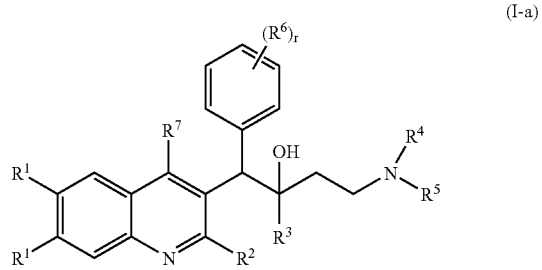

(I-a)

a pharmaceutically acceptable acid or base addition salt thereof, a stereochemically isomeric form thereof or a N-oxide form thereof.

3. The method according to claim 1 wherein the compound of formula (I) is a compound having the following formula

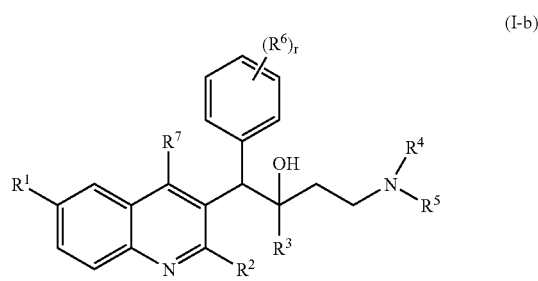

(I-b)

a pharmaceutically acceptable acid or base addition salt thereof, a stereochemically isomeric form thereof or a N-oxide form thereof.

4. The method according to claim 1 wherein $R^1$ is hydrogen, halo, optionally substituted phenyl, or Het.

5. According to claim 1 wherein $R^1$ is hydrogen, halo or optionally substituted phenyl.

6. The method according to claim 1 wherein $R^1$ is halo.

7. The method according to claim 1 wherein $R^2$ is $C_{1-6}$alkyloxy or $C_{1-6}$alkylthio.

8. The method according to claim 1 wherein $R^3$ is Ar or Het.

9. The method according to claim 1 wherein $R^3$ is Ar or Het¹.

10. The method according to claim 1 wherein $R^3$ is Ar.

11. The method according to claim 1 wherein $R^3$ is optionally substituted phenyl or optionally substituted naphthyl.

12. The method according to claim 1 wherein $R^4$ and $R^5$ each independently are hydrogen, $C_{1-6}$alkyl or benzyl.

13. The method according to claim 1 wherein $R^4$ and $R^5$ each independently are hydrogen or $C_{1-6}$alkyl.

14. The method according to claim 1 wherein $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, each of said rings may optionally be substituted with $C_{1-6}$alkyl, halo, polyhalo$C_{1-6}$alkyl, hydroxy, hydroxy$C_{1-6}$alkyl, $C_{1-6}$alkyloxy, amino, mono- or di($C_{1-6}$alkyl)amino, $C_{1-6}$alkylthio, $C_{1-6}$alkyloxy$C_{1-6}$alkyl, $C_{1-6}$alkylthio$C_{1-6}$alkyl or pyrimidinyl.

15. The method according to claim 1 wherein $R^4$ and $R^5$ together and including the N to which they are attached may form a radical selected from the group of pyrrolyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, each of said rings may optionally be substituted with $C_{1-6}$alkyl, halo, polyhalo$C_{1-6}$alkyl, hydroxy, hydroxy$C_{1-6}$alkyl, $C_{1-6}$alkyloxy, amino, mono- or di($C_{1-6}$alkyl)amino, $C_{1-6}$alkylthio, $C_{1-6}$alkyloxy$C_{1-6}$alkyl, $C_{1-6}$alkylthio$C_{1-6}$alkyl or pyrimidinyl.

16. The method according to claim 1 wherein $R^6$ is hydrogen, halo, polyhalo$C_{1-6}$alkyl, or $C_{1-6}$alkyl; or two vicinal $R^6$ radicals may be taken together to form a bivalent radical of formula —CH=CH—CH=CH—.

17. The method according to claim 1 wherein $R^6$ is hydrogen or halo.

18. The method according to claim 1 wherein $R^7$ is hydrogen.

19. The method according to claim 1 wherein r is an integer equal to 1.

20. The method according to claim 1 wherein p is an integer equal to 1.

21. The method according to claim 1 provided that when one $R^1$ is $C_{1-6}$alkyl then p is an integer equal to 2 and the other $R^1$ substituent is selected from halo, polyhalo$C_{1-6}$alkyl, $C_{1-6}$alkyl, Ar or Het.

22. The method according to claim 1 wherein the bacterial infection is an infection with a gram-positive bacterium.

23. The method according to claim 1 wherein $R^1$ is hydrogen; $C_{1-6}$alkyl; halo; phenyl; furanyl optionally substituted with hydroxy$C_{1-6}$alkyl; or pyridyl; $R^2$ is $C_{1-6}$alkyloxy; $C_{1-6}$alkylthio; or $C_{1-6}$alkyloxy$C_{1-6}$alkyloxy; $R^3$ is phenyl optionally substituted with 1 or 2 halo; naphthyl optionally substituted with 1 or 2 halo or $C_{1-6}$alkyloxy; thienyl; piperidinyl substituted with Ar—C(=O)—; 2,3-dihydrobenzo[1,4]dioxinyl; benzo[1,3]dioxolyl; or acenaphthyl; $R^4$ and $R^5$ are each independently hydrogen; $C_{1-6}$alkyl; benzyl; or $R^4$ and $R^5$ together and including the N to which they are attached may form a radical selected from imidazolyl; pyrazinyl substituted with $C_{1-6}$alkyl; piperazinyl substituted with $C_{1-6}$alkyl; piperazinyl substituted with pyrimidinyl; piperidinyl; thiomorpholinyl; morpholinyl; pyrrolidinyl; or triazolyl; $R^6$ is hydrogen; halo; $C_{1-6}$alkyl; or two vicinal $R^6$ radicals may be taken together to form a bivalent radical of formula —CH=CH—CH=CH—; $R^7$ is hydrogen.

24. The method according to claim 1 wherein $R^1$ is halo; $R^2$ is $C_{1-6}$alkyloxy or $C_{1-6}$alkylthio; $R^3$ is Ar; $R^4$ and $R^5$ each independently are hydrogen or $C_{1-6}$alkyl; $R^6$ is hydrogen or halo; $R^7$ is hydrogen; r is an integer equal to 1; p is an integer equal to 1.

25. The method according to claim 1 wherein the compound of formula (I) is selected from the following compounds

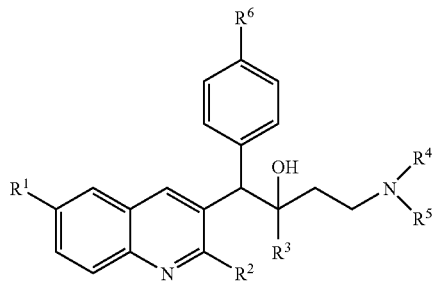

| $R^1$ | $R^2$ | $R^3$ | $R^4$ | $R^5$ | $R^6$ | Stereochemistry |
|---|---|---|---|---|---|---|
| Cl | OCH$_3$ | phenyl | CH$_3$ | CH$_3$ | H | mixture of 2 enantiomers having erythro/syn configuration |
| phenyl | OCH$_3$ | phenyl | CH$_3$ | CH$_3$ | H | mixture of 2 enantiomers having threo/anti configuration |
| Br | SCH$_3$ | phenyl | CH$_3$ | CH$_3$ | H | mixture of 2 enantiomers having erythro/syn configuration |
| Br | OCH$_3$ | 3-fluorophenyl | CH$_3$ | CH$_3$ | H | mixture of 2 enantiomers having erythro/syn configuration |
| Br | OCH$_3$ | phenyl | CH$_3$ | CH$_3$ | Cl | mixture of 2 enantiomers having erythro/syn |
| Br | OCH$_3$ | 2-naphthyl | CH$_3$ | CH$_3$ | H | mixture of 2 enantiomers having erythro/syn |
| Br | OCH$_3$ | 1-naphthyl | CH$_3$ | CH$_3$ | F | mixture of 2 enantiomers having erythro/syn configuration |
| Br | OCH$_3$ | phenyl | H | H | H | mixture of 2 enantiomers having threo/anti configuration |
| Br | OCH$_3$ | 2,4-difluorophenyl | H | CH$_2$CH$_3$ | H | mixture of 2 enantiomers having erythro/syn configuration |
| Br | OCH$_3$ | 1-naphthyl | CH$_3$ | CH$_3$ | H | (1S,2R) |
| Br | OCH$_3$ | phenyl | CH$_3$ | CH$_3$ | H | (1S,2S) |
| Br | OCH$_3$ | phenyl | CH$_3$ | CH$_3$ | H | (1R,2R) | a pharmaceutically acceptable acid or base addition salt thereof or a N-oxide form thereof.

26. A combination of (a) a compound of formula (I)

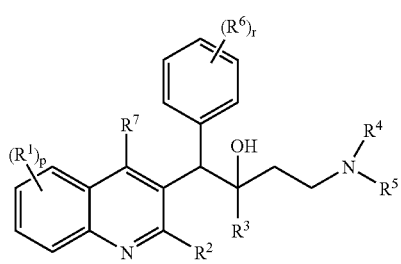

a pharmaceutically acceptable acid or base addition salt thereof, a stereochemically isomeric form thereof or a N-oxide form thereof, wherein $R^1$ is hydrogen, halo, polyhaloC$_{1-6}$alkyl, C$_{1-6}$alkyl, Ar or Het;

p is an integer equal to 1 or 2;

$R^2$ is C$_{1-6}$alkyloxy, C$_{1-6}$alkyloxyC$_{1-6}$alkyloxy or C$_{1-6}$alkylthio;

$R^3$ is Ar, Het or Het;

$R^4$ and $R^5$ each independently are hydrogen, C$_{1-6}$alkyl or benzyl; or $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, each of said rings may optionally be substituted with C$_{1-6}$alkyl, halo, polyhaloC$_{1-6}$alkyl, hydroxy, hydroxyC$_{1-6}$alkyl, C$_{1-6}$alkyloxy, amino, mono- or di(C$_{1-6}$alkyl)amino, C$_{1-6}$alkylthio, C$_{1-6}$alkyloxyC$_{1-6}$alkyl, C$_{1-6}$alkylthioC$_{1-6}$alkyl or pyrimidinyl;

$R^6$ is hydrogen, halo, polyhaloC$_{1-6}$alkyl, C$_{1-6}$alkyl, C$_{1-6}$alkyloxy, C$_{1-6}$alkylthio; or two vicinal $R^6$ radicals may be taken together to form a bivalent radical of formula —CH═CH—CH═CH—;

r is an integer equal to 1 or 2;

$R^7$ is hydrogen, C$_{1-6}$alkyl, Ar, Het or Het$^1$;

Ar is a homocycle selected from the group of phenyl, naphthyl, acenaphthyl, tetrahydronaphthyl, each homocycle may optionally be substituted with 1, 2 or 3 substituents, each substituent independently selected from the group of hydroxy, halo, cyano, nitro, amino, mono- or di(C$_{1-6}$alkyl)amino, C$_{1-6}$alkyl, polyhaloC$_{1-6}$alkyl, hydroxyC$_{1-6}$alkyl, C$_{1-6}$alkyloxy, polyhaloC$_{1-6}$alkyloxy, C$_{1-6}$alkyloxyC$_{1-6}$alkyl, carboxyl, C$_{1-6}$alkyloxycarbonyl, aminocarbonyl, morpholinyl and mono- or di(C$_{1-6}$alkyl)aminocarbonyl;

Het is a monocyclic heterocycle selected from the group of N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; each monocyclic heterocycle may optionally be substituted with 1, 2 or 3 substituents, each substituent independently selected from the group of halo, hydroxy, $C_{1-6}$alkyl, polyhalo$C_{1-6}$alkyl, hydroxy$C_{1-6}$alkyl, $C_{1-6}$alkyloxy, $C_{1-6}$alkyloxy$C_{1-6}$alkyl or Ar—C(=O)—;

Het$^1$ is a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each bicyclic heterocycle may optionally be substituted with 1, 2 or 3 substituents, each substituent independently selected from the group of halo, hydroxy, $C_{1-6}$alkyl, polyhalo$C_{1-6}$alkyl, hydroxy$C_{1-6}$alkyl, $C_{1-6}$alkyloxy, $C_{1-6}$alkyloxy$C_{1-6}$alkyl or Ar—C(=O)—; and (b) one or more other antibacterial agents provided that the one or more other antibacterial agents are other than antimycobacterial agents.

27. A pharmaceutical composition comprising a pharmaceutically acceptable carrier and, as active ingredient, a therapeutically effective amount of (a) a compound of formula (I)

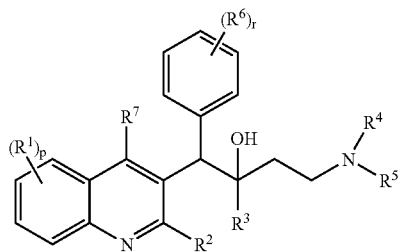

(I)

a pharmaceutically acceptable acid or base addition salt thereof, a stereochemically isomeric form thereof or a N-oxide form thereof, wherein $R^1$ is hydrogen, halo, polyhalo$C_{1-6}$alkyl, $C_{1-6}$alkyl, Ar or Het;

p is an integer equal to 1 or 2;

$R^2$ is $C_{1-6}$alkyloxy, $C_{1-6}$alkyloxy$C_{1-6}$alkyloxy or $C_{1-6}$alkylthio;

$R^3$ is Ar, Het or Het$^1$;

$R^4$ and $R^5$ each independently are hydrogen, $C_{1-6}$alkyl or benzyl; or $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, each of said rings may optionally be substituted with $C_{1-6}$alkyl, halo, polyhalo$C_{1-6}$alkyl, hydroxy, hydroxy$C_{1-6}$alkyl, $C_{1-6}$alkyloxy, amino, mono- or di($C_{1-6}$alkyl)amino, $C_{1-6}$alkylthio, $C_{1-6}$alkyloxy$C_{1-6}$alkyl, $C_{1-6}$alkylthio$C_{1-6}$alkyl or pyrimidinyl;

$R^6$ is hydrogen, halo, polyhalo$C_{1-6}$alkyl, $C_{1-6}$alkyl, $C_{1-6}$alkyloxy, $C_{1-6}$alkylthio; or two vicinal $R^6$ radicals may be taken together to form a bivalent radical of formula —CH=CH—CH=CH—;

r is an integer equal to 1 or 2;

$R^7$ is hydrogen, $C_{1-6}$alkyl, Ar, Het or Het$^1$;

Ar is a homocycle selected from the group of phenyl, naphthyl, acenaphthyl, tetrahydronaphthyl, each homocycle may optionally be substituted with 1, 2 or 3 substituents, each substituent independently selected from the group of hydroxy, halo, cyano, nitro, amino, mono- or di($C_{1-6}$alkyl)amino, $C_{1-6}$alkyl, polyhalo$C_{1-6}$alkyl, hydroxy$C_{1-6}$alkyl, $C_{1-6}$alkyloxy, polyhalo$C_{1-6}$alkyloxy, $R^1$ is hydrogen, halo, polyhalo$C_{1-6}$alkyl, $C_{1-6}$alkyl, Ar or Het;

p is an integer equal to 1 or 2;

$R^2$ is $C_{1-6}$alkyloxy, $C_{1-6}$alkyloxy$C_{1-6}$alkyloxy or $C_{1-6}$alkylthio;

$R^3$ is Ar, Het or Het$^1$;

$R^4$ and $R^5$ each independently are hydrogen, $C_{1-6}$alkyl or benzyl; or $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, each of said rings may optionally be substituted with $C_{1-6}$alkyl, halo, polyhalo$C_{1-6}$alkyl, hydroxy, hydroxy$C_{1-6}$alkyl, $C_{1-6}$alkyloxy, amino, mono- or di($C_{1-6}$alkyl)amino, $C_{1-6}$alkylthio, $C_{1-6}$alkyloxy$C_{1-6}$alkyl, $C_{1-6}$alkylthio$C_{1-6}$alkyl or pyrimidinyl;

$R^6$ is hydrogen, halo, polyhalo$C_{1-6}$alkyl, $C_{1-6}$alkyl, $C_{1-6}$alkyloxy, $C_{1-6}$alkylthio; or two vicinal $R^6$ radicals may be taken together to form a bivalent radical of formula —CH=CH—CH=CH—;

r is an integer equal to 1 or 2;

$R^7$ is hydrogen, $C_{1-6}$alkyl, Ar, Het or Het$^1$;

Ar is a homocycle selected from the group of phenyl, naphthyl, acenaphthyl, tetrahydronaphthyl, each homocycle may optionally be substituted with 1, 2 or 3 substituents, each substituent independently selected from the group of hydroxy, halo, cyano, nitro, amino, mono- or di($C_{1-6}$alkyl)amino, $C_{1-6}$alkyl, polyhalo$C_{1-6}$alkyl, hydroxy$C_{1-6}$alkyl, $C_{1-6}$alkyloxy, polyhalo$C_{1-6}$alkyloxy, $C_{1-6}$alkyloxy$C_{1-6}$alkyl, carboxyl, $C_{1-6}$alkyloxycarbonyl, aminocarbonyl, morpholinyl and mono- or di($C_{1-6}$alkyl)aminocarbonyl;

Het is a monocyclic heterocycle selected from the group of N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; each monocyclic heterocycle may optionally be substituted with 1, 2 or 3 substituents, each substituent independently selected from the group of halo, hydroxy, $C_{1-6}$alkyl, polyhalo$C_{1-6}$alkyl, hydroxy$C_{1-6}$alkyl, $C_{1-6}$alkyloxy, $C_{1-6}$alkyloxy$C_{1-6}$alkyl or Ar—C(=O)—;

Het$^1$ is a bicyclic heterocycle selected from the group of quinolinyl, quinoxalinyl, indolyl, benzimidazolyl, benzoxazolyl, benzisoxazolyl, benzothiazolyl, $C_{1-6}$alkyloxy$C_{1-6}$alkyl, carboxyl, $C_{1-6}$alkyloxycarbonyl, aminocarbonyl, morpholinyl and mono- or di($C_{1-6}$alkyl)aminocarbonyl;

Het is a monocyclic heterocycle selected from the group of N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; each monocyclic heterocycle may optionally be substituted with 1, 2 or 3 substituents, each substituent independently selected from the group of halo, hydroxy, $C_{1-6}$alkyl, polyhalo$C_{1-6}$alkyl, hydroxy$C_{1-6}$alkyl, $C_{1-6}$alkyloxy, $C_{1-6}$alkyloxy$C_{1-6}$alkyl or Ar—C(=O)—;

Het$^1$ is a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each bicyclic heterocycle may optionally be substituted with 1, 2 or 3 substituents, each substituent independently selected from the group of halo, hydroxy, $C_{1-6}$alkyl, polyhalo $C_{1-6}$alkyl, hydroxy$C_{1-6}$alkyl, $C_{1-6}$alkyloxy, $C_{1-6}$alkyloxy$C_{1-6}$alkyl or Ar—C(=O)—; and (b) one or more other antibacterial agents provided that the one or more other antibacterial agents are other than antimycobacterial agents.

28. A product containing (a) a compound of formula (I)

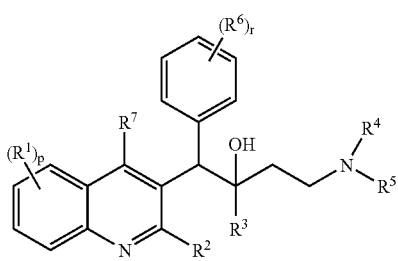

(I)

a pharmaceutically acceptable acid or base addition salt thereof, a stereochemically isomeric form thereof or a N-oxide form thereof, wherein benzisothiazolyl, benzofuranyl, benzothienyl, 2,3-dihydrobenzo[1,4]dioxinyl or benzo[1,3]dioxolyl each bicyclic heterocycle may optionally be substituted with 1, 2 or 3 substituents, each substituent independently selected from the group of halo, hydroxy, $C_{1-6}$alkyl, polyhalo$C_{1-6}$alkyl, hydroxy$C_{1-6}$alkyl, $C_{1-6}$alkyloxy, $C_{1-6}$alkyloxy$C_{1-6}$alkyl or Ar—C(=O)—; and (b) one or more other antibacterial agents provided that the one or more other antibacterial agents are other than antimycobacterial agents, as a combined preparation for simultaneous, separate or sequential use in the treatment of a bacterial infection.

29. The method according to claim 1 wherein the compound of formula I is selected from the following compounds

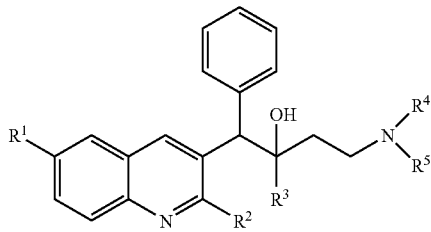

| $R^1$ | $R^2$ | $R^3$ | $R^4$ | $R^5$ | Stereochemistry |
|---|---|---|---|---|---|
| Br | OCH$_3$ | 2,4-difluorophenyl | H | CH$_2$CH$_3$ | mixture of 2 enantiomers having erythro/syn configuration |
| Br | OCH$_3$ | 2,4-difluorophenyl | H | CH$_2$CH$_3$ | mixture of 2 enantiomers having threo/anti configuration |
| Br | OCH$_3$ | 2,4-difluorophenyl | CH$_2$CH$_3$ | benzyl | mixture of 2 enantiomers having erythro/syn configuration |
| Br | OCH$_3$ | phenyl | H | CH$_3$ | mixture of 2 enantiomers having erythro/syn configuration |
| Br | OCH$_3$ | phenyl | CH$_3$ | CH$_3$ | (1S,2S) |
| Br | OCH$_3$ | phenyl | CH$_3$ | CH$_3$ | (1R,2R) |
| 3-pyridyl | OCH$_3$ | 3,5-difluorophenyl | CH$_3$ | CH$_3$ | mixture of 2 enantiomers having threo/anti configuration |
| 2-furanyl | OCH$_3$ | 1-naphthyl | CH$_3$ | CH$_3$ | mixture of 2 enantiomers having erythro/syn configuration |
| Br | OCH$_3$ | 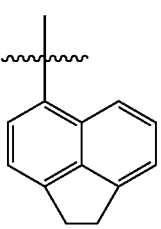 | CH$_3$ | CH$_3$ | mixture of 2 enantiomers having threo/anti configuration | a pharmaceutically acceptable acid or base addition salt thereof or a N-oxide form thereof.

30. The method according to claim 1 wherein the bacterial infection is selected from the group consisting of an infection with staphylococci, enterococci and streptococci.

31. The method according to claim 1 wherein the bacterial infection is selected from the group consisting of an infection with methicillin resistant *staphylococcus aureus* (MRSA), methicillin resistant coagulase negative staphylococci (MRCNS), penicillin resistant *Streptococcus pneumoniae* and multiple resistant *enterococcus faecium*.

32. The method according to claim 1 wherein the bacterial infection is selected from the group consisting of an infection with *staphylococcus aureus* and *streptococcus pneumoniae*.

33. The method according to claim 1 wherein the bacterial infection is an infection with methicillin resistant *staphylococcus aureus* (MRSA).

34. A method for the treatment of a person suffering from a bacterial infection which comprises administering to said patient a therapeutically effective amount of a combination as claimed in claim 26 provided that the bacterial infection is other than a Mycobacterial infection.

35. A method for the treatment of a person suffering from a bacterial infection, which comprises administering to said patient a therapeutically effective amount of a pharmaceutical composition as claimed in claim 27 provided that the bacterial infection is other than a Mycobacterial infection.

* * * * *